US010828401B2

(12) United States Patent
Gregory et al.

(10) Patent No.: US 10,828,401 B2
(45) Date of Patent: Nov. 10, 2020

(54) SYSTEMS AND METHODS FOR APPLYING REDUCED NEGATIVE PRESSURE THERAPY

(71) Applicant: Smith & Nephew, Inc., Memphis, TN (US)

(72) Inventors: William W. Gregory, Gainesville, FL (US); William Joseph Jaecklein, Saint Petersburg, FL (US); Felix C. Quintanar, Hull (GB); Matthew T. Smith, Raleigh, NC (US)

(73) Assignee: Smith & Nephew, Inc., Memphis, TN (US)

( * ) Notice: Subject to any disclaimer, the term of this patent is extended or adjusted under 35 U.S.C. 154(b) by 339 days.

(21) Appl. No.: 15/757,467

(22) PCT Filed: Oct. 22, 2015

(86) PCT No.: PCT/US2015/057011
§ 371 (c)(1),
(2) Date: Mar. 5, 2018

(87) PCT Pub. No.: WO2017/044138
PCT Pub. Date: Mar. 16, 2017

(65) Prior Publication Data
US 2018/0264181 A1 Sep. 20, 2018

Related U.S. Application Data

(60) Provisional application No. 62/217,517, filed on Sep. 11, 2015.

(51) Int. Cl.
*A61M 1/00* (2006.01)
*A61F 13/00* (2006.01)
(Continued)

(52) U.S. Cl.
CPC ..... *A61M 1/0025* (2014.02); *A61F 13/00068* (2013.01); *A61M 1/0031* (2013.01);
(Continued)

(58) Field of Classification Search
CPC .......... A61M 1/00; A61M 5/178; A61M 5/00; A61M 5/32; A61M 35/00; A61F 13/00
See application file for complete search history.

(56) References Cited

U.S. PATENT DOCUMENTS 5,419,768 A  5/1995  Kayser
5,599,308 A  2/1997  Krupa
(Continued)

FOREIGN PATENT DOCUMENTS

EP  2175906  *  6/2008
EP  2 175 906 A2  4/2010
(Continued)

OTHER PUBLICATIONS

International Search Report and Written Opinion, International App. No. PCT/US2015/057011, filed on Oct. 22, 2015, dated May 24, 2016 in 15 pages.
(Continued)

Primary Examiner — Tatyana Zalukaeva
Assistant Examiner — Ilya Y Treyger
(74) Attorney, Agent, or Firm — Knobbe, Martens, Olson & Bear, LLP

(57) ABSTRACT

Embodiments of a negative pressure wound therapy systems and methods for operating the systems are disclosed. In some embodiments, a system includes a pump assembly, canister, and a wound dressing configured to be positioned over a wound. The pump assembly, canister, and the wound dressing can be fluidically connected to facilitate delivery of negative pressure to a wound. The system can be configured to efficiently deliver negative pressure in continuous and
(Continued)

intermittent modes. The system can also be configured to gradually ramp up and down to set pressure values. The system can also be configured to detect and indicate presence of certain conditions, such as low pressure, high pressure, leak, canister full, and the like. Detection and indication of the presence of at least some of these conditions can be enabled and disabled.

20 Claims, 24 Drawing Sheets

(51) Int. Cl.
    *A61M 5/00*     (2006.01)
    *A61M 5/32*     (2006.01)
    *A61M 35/00*     (2006.01)

(52) U.S. Cl.
    CPC ........ *A61M 1/0037* (2013.01); *A61M 1/0088* (2013.01); *A61M 2205/3331* (2013.01); *A61M 2205/3344* (2013.01)

(56) References Cited

U.S. PATENT DOCUMENTS

| | | |
|---|---|---|
| 6,228,056 B1 | 5/2001 | Boehringer et al. |
| 7,004,915 B2 | 2/2006 | Boynton et al. |
| 7,022,113 B2 | 4/2006 | Lockwood et al. |
| 7,438,705 B2 | 10/2008 | Karpowicz et al. |
| 7,553,306 B1 | 6/2009 | Hunt et al. |
| 7,670,323 B2 | 3/2010 | Hunt et al. |
| 7,753,894 B2 | 7/2010 | Blott et al. |
| 8,235,955 B2 | 8/2012 | Blott et al. |
| 8,366,692 B2 | 2/2013 | Weston |
| 8,377,016 B2 | 2/2013 | Argenta et al. |
| 8,444,392 B2 | 5/2013 | Turner et al. |
| 8,494,349 B2 | 7/2013 | Gordon |
| 8,535,296 B2 | 9/2013 | Blott et al. |
| 8,540,688 B2 | 9/2013 | Eckstein et al. |
| 8,791,316 B2 | 7/2014 | Greener |
| 8,905,985 B2 | 12/2014 | Allen et al. |
| 9,019,681 B2 | 4/2015 | Locke et al. |
| 9,023,002 B2 | 5/2015 | Robinson et al. |
| 9,067,003 B2 | 6/2015 | Buan et al. |
| 9,220,822 B2 | 12/2015 | Hartwell et al. |
| 9,408,954 B2 | 8/2016 | Gordon et al. |
| 2001/0049609 A1 | 12/2001 | Girouard et al. |
| 2004/0064132 A1 | 4/2004 | Boehringer et al. |
| 2006/0029675 A1 | 2/2006 | Ginther |
| 2006/0149171 A1 | 7/2006 | Vogel et al. |
| 2007/0118096 A1 | 5/2007 | Smith et al. |
| 2008/0039761 A1 | 2/2008 | Heaton et al. |
| 2008/0041401 A1* | 2/2008 | Casola ................ A61M 1/0031 128/897 |
| 2008/0177224 A1 | 7/2008 | Kelly et al. |
| 2008/0208147 A1 | 8/2008 | Argenta et al. |
| 2009/0043268 A1 | 2/2009 | Eddy et al. |
| 2009/0082741 A1 | 3/2009 | Hu |
| 2009/0171288 A1 | 7/2009 | Wheeler |
| 2009/0182266 A1 | 7/2009 | Gordon et al. |
| 2009/0299306 A1 | 12/2009 | Buan |
| 2010/0022990 A1 | 1/2010 | Karpowicz et al. |
| 2010/0042059 A1 | 2/2010 | Pratt et al. |
| 2010/0145289 A1 | 6/2010 | Line et al. |
| 2010/0150991 A1 | 6/2010 | Bernstein |
| 2010/0168687 A1 | 7/2010 | Yu |
| 2010/0228205 A1 | 9/2010 | Hu et al. |
| 2010/0274177 A1 | 10/2010 | Rybski et al. |
| 2011/0015585 A1 | 1/2011 | Svedman et al. |
| 2011/0063117 A1 | 3/2011 | Turner |
| 2011/0066096 A1 | 3/2011 | Svedman |
| 2011/0112492 A1 | 5/2011 | Bharti et al. |
| 2011/0257572 A1 | 10/2011 | Locke et al. |
| 2012/0001762 A1 | 1/2012 | Turner et al. |
| 2012/0035560 A1 | 2/2012 | Eddy et al. |
| 2012/0046625 A1 | 2/2012 | Johannison |
| 2012/0184930 A1 | 7/2012 | Johannison |
| 2012/0271256 A1 | 10/2012 | Locke et al. |
| 2012/0289914 A1 | 11/2012 | Eckstein et al. |
| 2013/0019744 A1 | 1/2013 | Hu |
| 2013/0245580 A1 | 9/2013 | Locke et al. |
| 2013/0267919 A1 | 10/2013 | Caso et al. |
| 2013/0303975 A1 | 11/2013 | Gvodas et al. |
| 2013/0310781 A1 | 11/2013 | Phillips et al. |
| 2013/0317463 A1 | 11/2013 | Yao et al. |
| 2013/0327326 A1 | 12/2013 | Brennan |
| 2014/0350494 A1 | 11/2014 | Hartwell et al. |
| 2015/0159066 A1 | 6/2015 | Hartwell et al. |

FOREIGN PATENT DOCUMENTS

| | | |
|---|---|---|
| EP | 2 529 765 | 12/2012 |
| EP | 2 389 961 | 3/2013 |
| WO | WO 2008/104609 | 9/2008 |
| WO | WO 2008/132215 | 11/2008 |
| WO | WO2009089390 * | 1/2009 |
| WO | WO 2009/021523 | 2/2009 |
| WO | WO 2009/089390 A2 | 7/2009 |
| WO | WO 2009/093116 | 7/2009 |
| WO | WO 2011/023275 | 3/2011 |
| WO | WO 2013/014278 | 1/2013 |
| WO | WO 2013/123022 | 8/2013 |
| WO | WO 2016/018448 A1 | 2/2016 |
| WO | WO 2017/044138 | 3/2017 |

OTHER PUBLICATIONS

International Preliminary Report on Patentability, re PCT Application No. PCT/US2015/057011, dated Mar. 22, 2018.
"Vivano—Product application description," Hartmann Vivano, http://www.vivanosystem.info/20809.php, accessed Feb. 28, 2013.

* cited by examiner

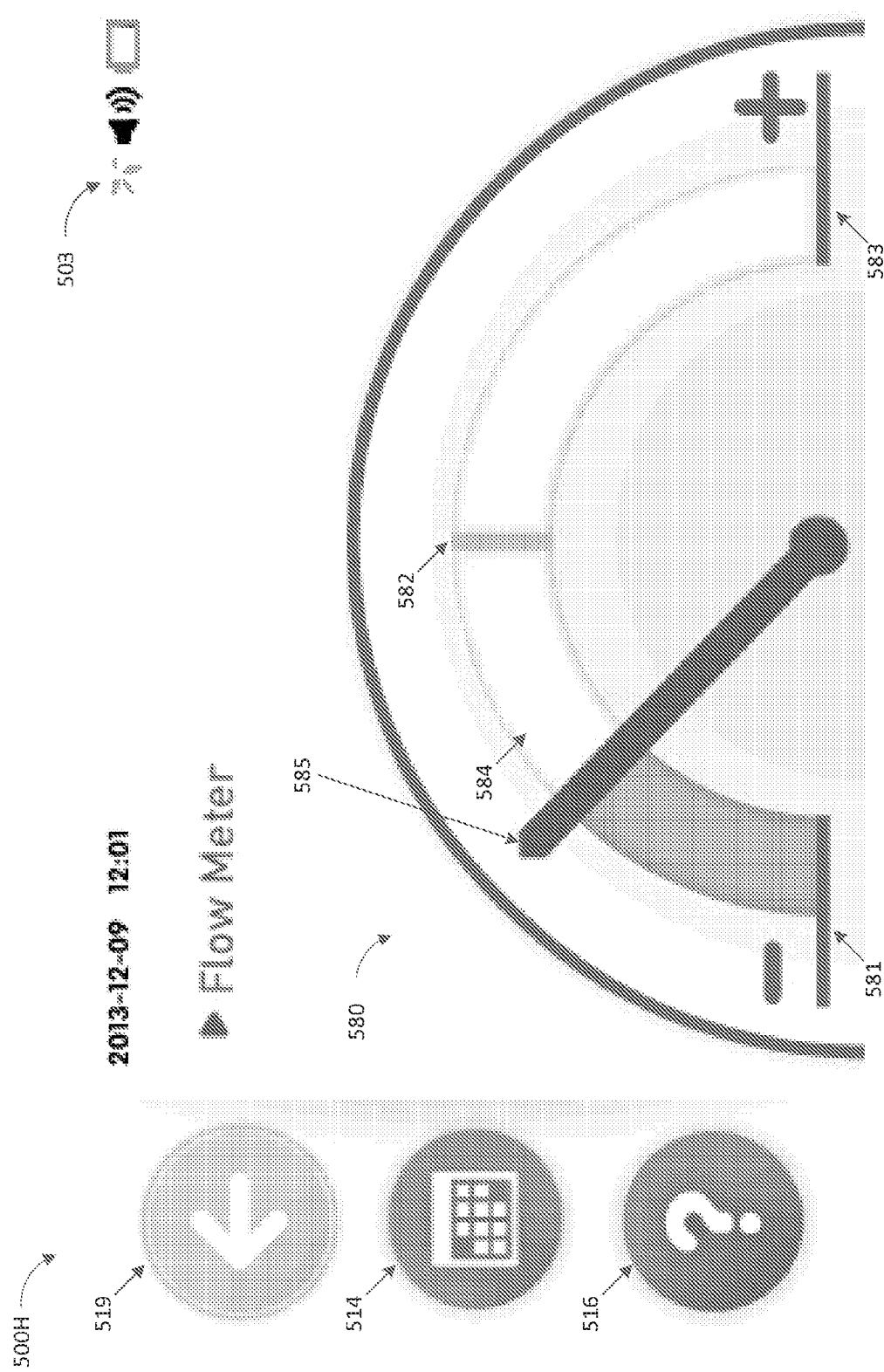

SYSTEMS AND METHODS FOR APPLYING REDUCED NEGATIVE PRESSURE THERAPY

BACKGROUND

Field

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TMP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema, encouraging blood flow, stimulating the formation of granulation tissue, removing excess exudates and may reduce bacterial load and, thus, infection to the wound. Furthermore, TNP therapy permits less outside disturbance of the wound and promotes more rapid healing.

SUMMARY

In some embodiments, an apparatus for applying negative pressure therapy to a wound includes a source of negative pressure configured to be in fluidic communication with a wound dressing and configured to aspirate fluid from the wound, a pressure sensor configured to measure pressure under the wound dressing, and a controller configured to operate the source of negative pressure to reach a pressure setting under the wound dressing. The controller can be further configured to determine a pressure difference between current pressure under the wound dressing measured by the pressure sensor and the pressure setting, wherein the pressure setting is more positive than the current pressure under the wound dressing, and based on the pressure difference and a compression setting, operate the source of negative pressure to attain the pressure setting under the wound dressing.

In some embodiments, the apparatus of the preceding paragraph can include one or more of the following features. The controller can be further configured to determine an intermediate pressure setting that is more positive than the current pressure and more negative than the pressure setting and operate the source of negative pressure to attain the intermediate pressure setting under the wound dressing. The controller can be further configured to determine a pressure increment based on the compression setting and set the intermediate pressure setting to a sum of the current pressure and the pressure increment. The controller can be further configured to in response to determining that the current intermediate pressure setting has been achieved under the wound dressing, update the intermediate pressure setting to be equal to a sum of previous intermediate pressure setting and the pressure increment. The controller can be further configured to in response to determining that the current intermediate pressure setting has been achieved under the wound dressing, redetermine the pressure increment and update the intermediate pressure setting to be equal to a sum of previous intermediate pressure setting and the updated pressure increment. The controller can be further configured to turn off the source of negative pressure for a duration of time, the duration of time based on the compression setting. The compression setting can be selected by a user.

In some embodiments, a method of operating a negative pressure apparatus includes measuring pressure under a wound dressing configured to be positioned over a wound, determining a pressure difference between current pressure under the wound dressing and a pressure setting, wherein the pressure setting is more positive than the current pressure under the wound dressing, and based on the pressure difference and a compression setting, providing negative pressure to the wound dressing to attain the pressure setting under the wound dressing.

In some embodiments, the method of the preceding paragraph can include one or more of the following features. The method can further include determining an intermediate pressure setting that is more positive than the current pressure and more negative than the pressure setting and providing negative pressure to the wound dressing to attain the intermediate pressure setting under the wound dressing. The method can further include determining a pressure increment based on the compression setting and setting the intermediate pressure setting to a sum of the current pressure and the pressure increment. The method can further include in response to determining that the current intermediate pressure setting has been achieved under the wound dressing, updating the intermediate pressure setting to be equal to a sum of previous intermediate pressure setting and the pressure increment. The method can further include in response to determining that the current intermediate pressure setting has been achieved under the wound dressing, redetermining the pressure increment and updating the intermediate pressure setting to be equal to a sum of previous intermediate pressure setting and the updated pressure increment. The method can further include stopping provision of negative pressure to the wound for a duration of time, the duration of time based on the compression setting. The compression setting can be selected by a user.

In some embodiments, an apparatus for applying negative pressure therapy to a wound includes a source of negative pressure configured to be in fluidic communication with a wound dressing via a fluid flow path, the source of negative pressure configured to aspirate fluid from the wound and a controller configured to operate the source of negative pressure. The controller can be further configured to deactivate detection of a presence of a condition in the fluid flow path, in response to occurrence of an event, activate detection of the presence of the condition in the fluid flow path, and in response to detecting the presence of the condition in the fluid flow path, provide an indication of the presence of the condition.

In some embodiments, the apparatus of the preceding paragraph can include one or more of the following features. The apparatus can include a canister positioned in the fluid flow path and configured to store at least some of the aspirated fluid. The condition can include one of a blockage in the fluid flow path, a leak in the fluid flow path, low pressure in the fluid flow path, high pressure in the fluid flow path, or a canister full. The controller can be further configured to deactivate the detection while the negative pressure source is activated to provide a negative pressure level under the wound dressing. The event can include reaching a steady state pressure under the wound dressing.

BRIEF DESCRIPTION OF THE DRAWINGS

Embodiments of the present invention will now be described hereinafter, by way of example only, with reference to the accompanying drawings in which:

FIGS. 5A-5I illustrate graphical user interface screens according to some embodiments.

DETAILED DESCRIPTION OF SOME EMBODIMENTS

Overview

Embodiments disclosed herein relate to systems and methods of treating a wound with reduced pressure. As is used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects absolute pressure that is X mmHg below 760 mmHg or, in other words, an absolute pressure of (760–X) mmHg. In addition, negative pressure that is "less" or "smaller" than X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg). In some embodiments, local ambient atmospheric pressure is used as a reference point, and such local atmospheric pressure may not necessarily be, for example, 760 mmHg.

Embodiments of the present invention are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
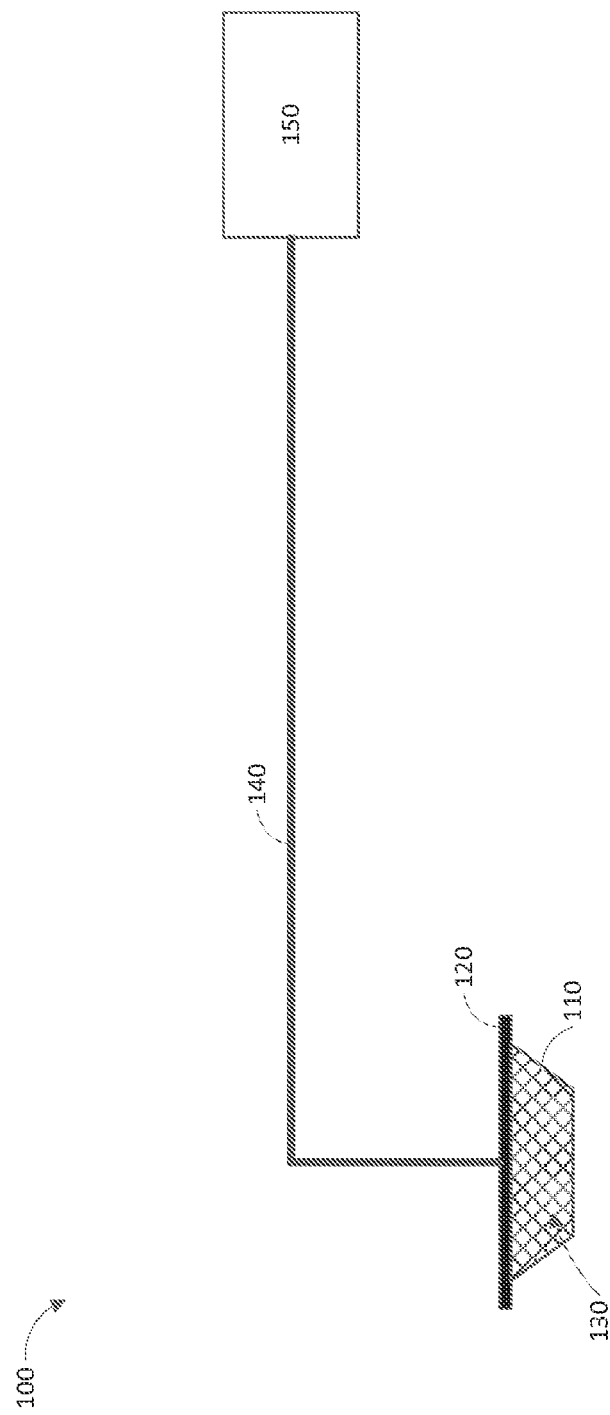
FIG. 1 illustrates a reduced pressure wound therapy system according to some embodiments.

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure setpoints. Low setpoint can be set at 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High setpoint can be set at −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low setpoint can be delivered for a first time duration, and upon expiration of the first time duration, negative pressure at high setpoint can be delivered for a second time duration. Upon expiration of the second time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Pump Assembly and Canister

Figure 2A:
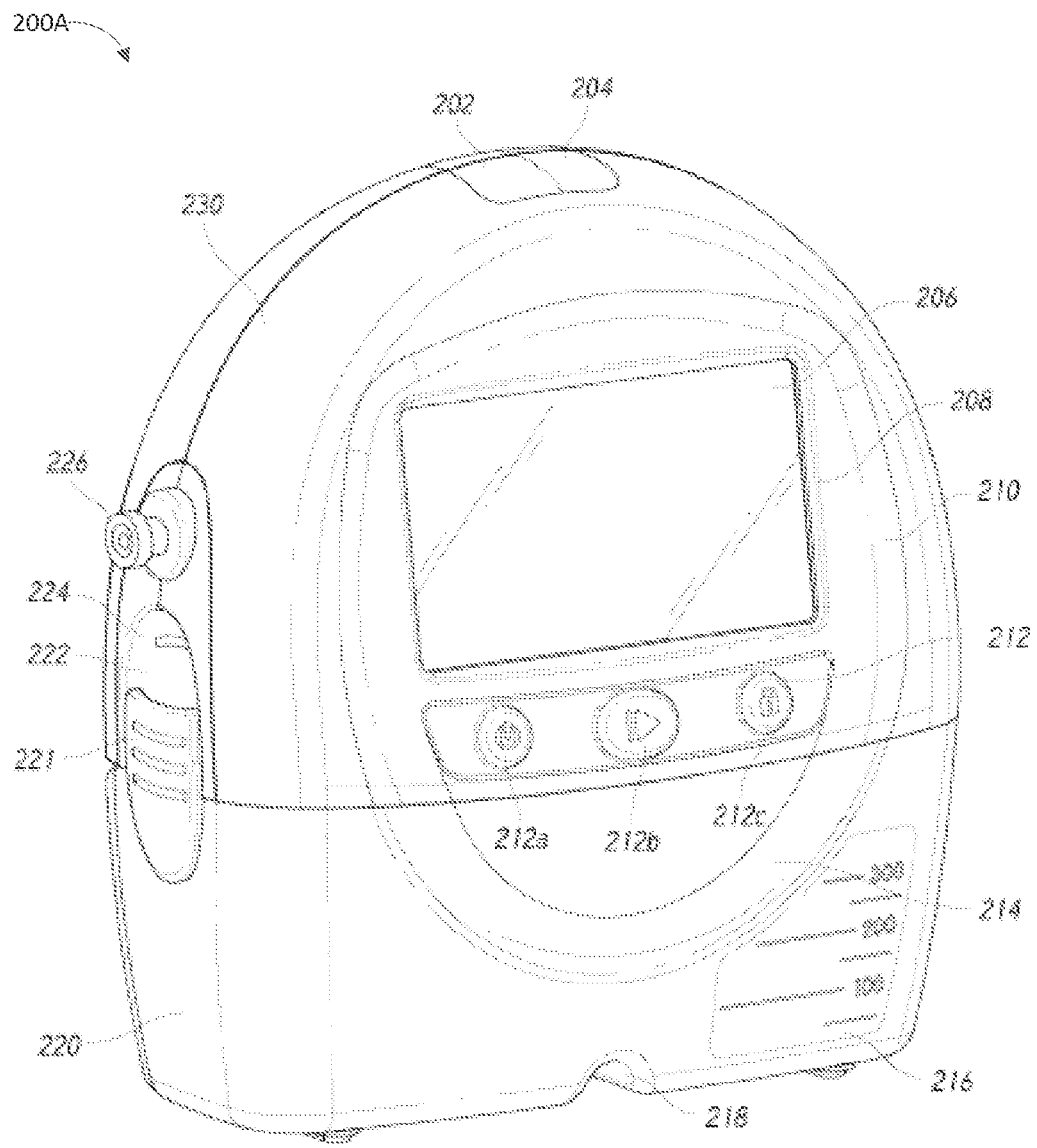
FIGS. 2A-2C illustrate a pump assembly and canister according to some embodiments.

FIG. 2A illustrates a front view 200A of a pump assembly 230 and canister 220 according to some embodiments. As is illustrated, the pump assembly 230 and the canister are connected, thereby forming a device. The pump assembly 230 comprises one or more indicators, such as visual indicator 202 configured to indicate alarms and visual indicator 204 configured to indicate status of the TNT system. The indicators 202 and 204 can be configured to alert a user, such as patient or medical care provider, to a variety of operating and/or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 comprises a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 comprises one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212*b* can cause therapy to start, and pressing the button 212*b* afterward can cause therapy to pause or end. Button 212*c* can be configured to lock the display 206 and/or the buttons 212. For instance, button 212*c* can be pressed so that the user does not unintentionally alter the delivery of the therapy. Button 212*c* can be depressed to unlock the controls. In other embodiments, additional buttons can be used or one or more of the illustrated buttons 212*a*, 212*b*, or 212*c* can be omitted. Multiple key presses and/or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted and/or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted and/or various additional features are added to the canister 220. Any of the disclosed canisters may include or may omit a solidifier.

Figure 2B:
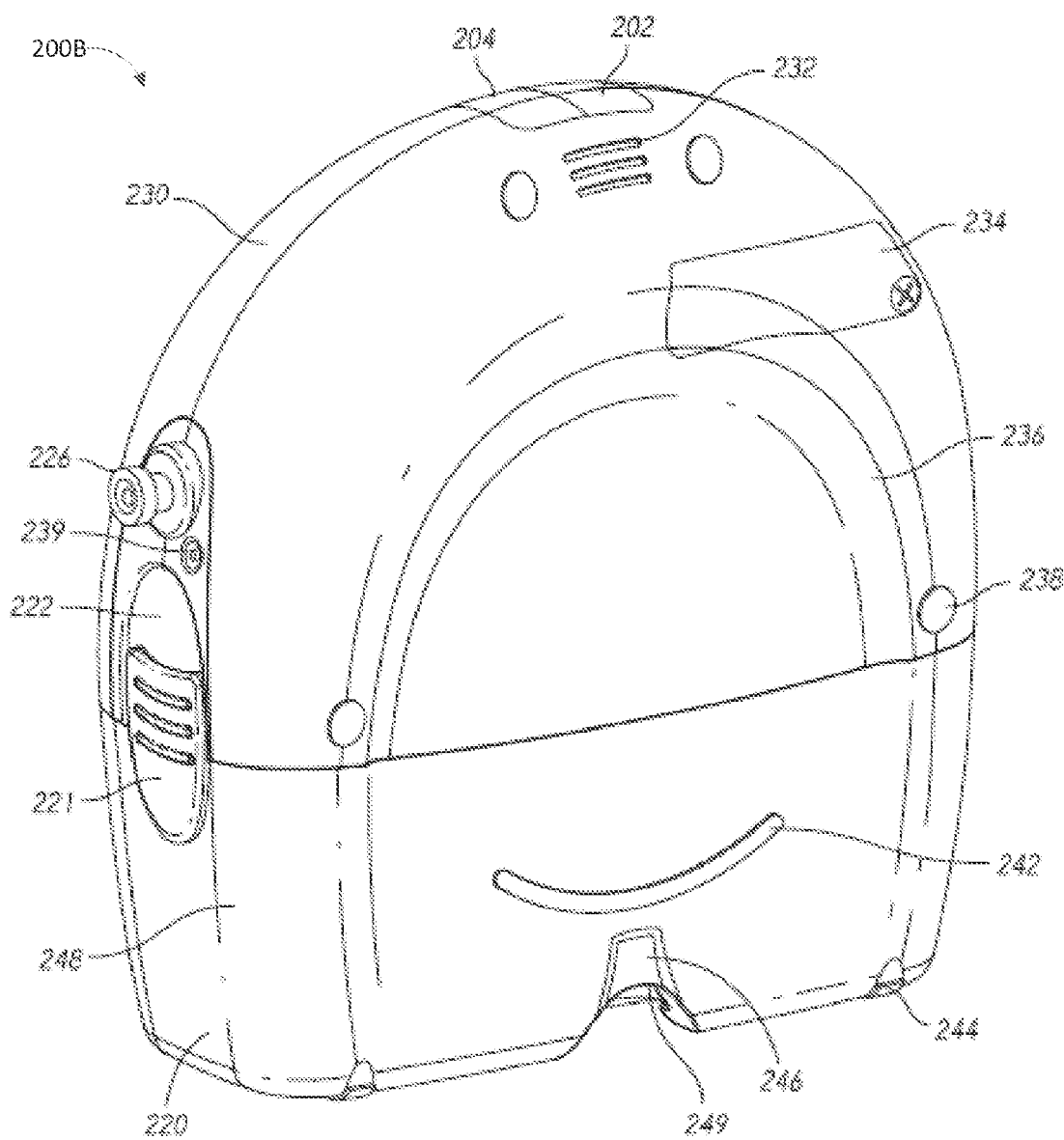

FIG. 2B illustrates a rear view 200B of the pump assembly 230 and canister 220 according to some embodiments. The pump assembly 230 comprises a speaker port 232 for producing sound. The pump assembly 230 includes a filter access door 234 for accessing and replacing one or more filters, such as antibacterial filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers and/or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
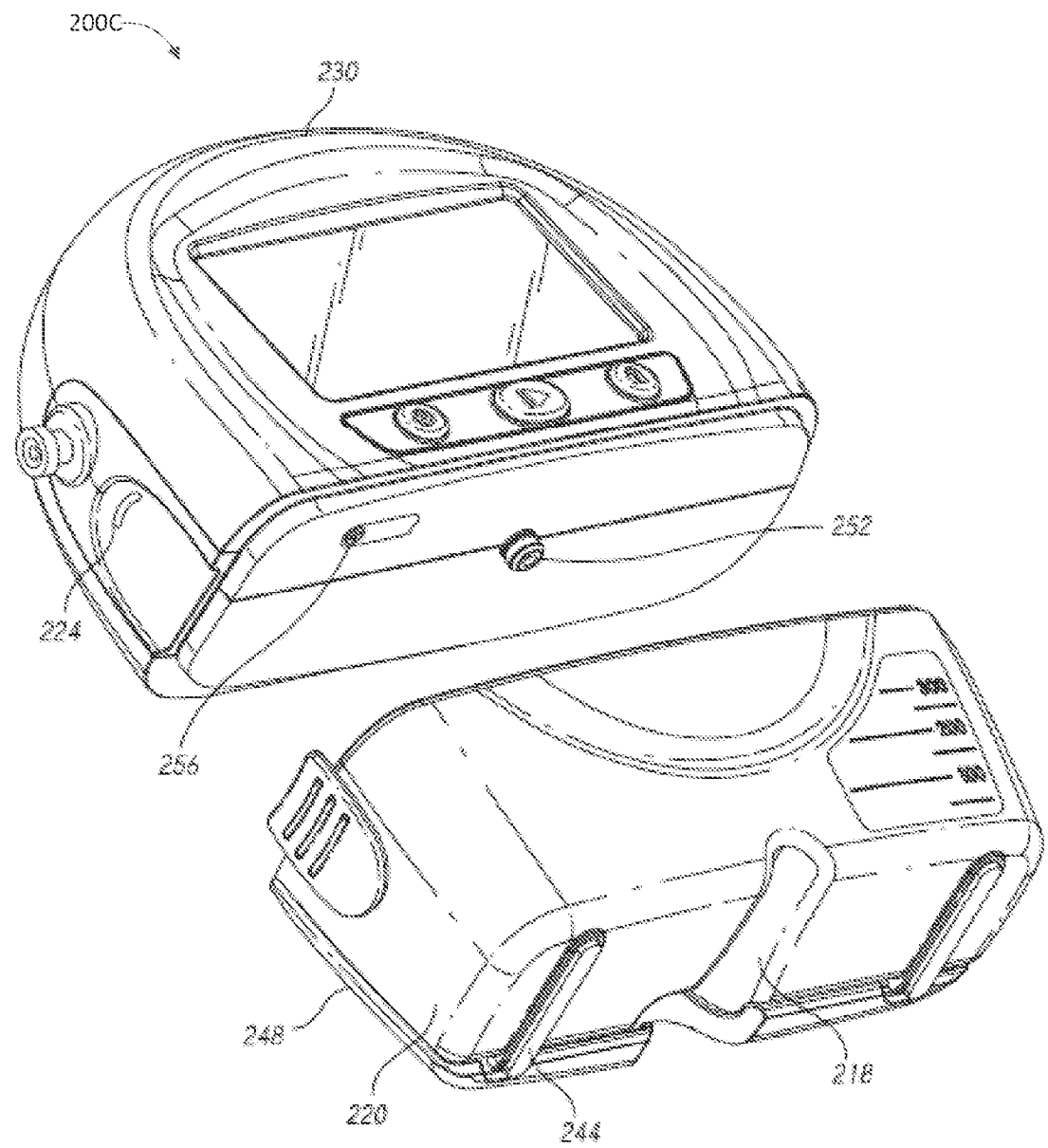

FIG. 2C illustrates a view 200C of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, and/or hybrid data transfer interfaces, such as SD, Compact Disc (CD), END, FireWire, Thunderbolt, PCI Express, and the like. In other embodiments, one or more of these additional ports are accessed through the door 234.

Additional description of the pump assembly is disclosed in U.S. Patent Application Publication No. 2015/0025482, which is incorporated by reference in its entirety.

Electronics and Software

Figure 3:
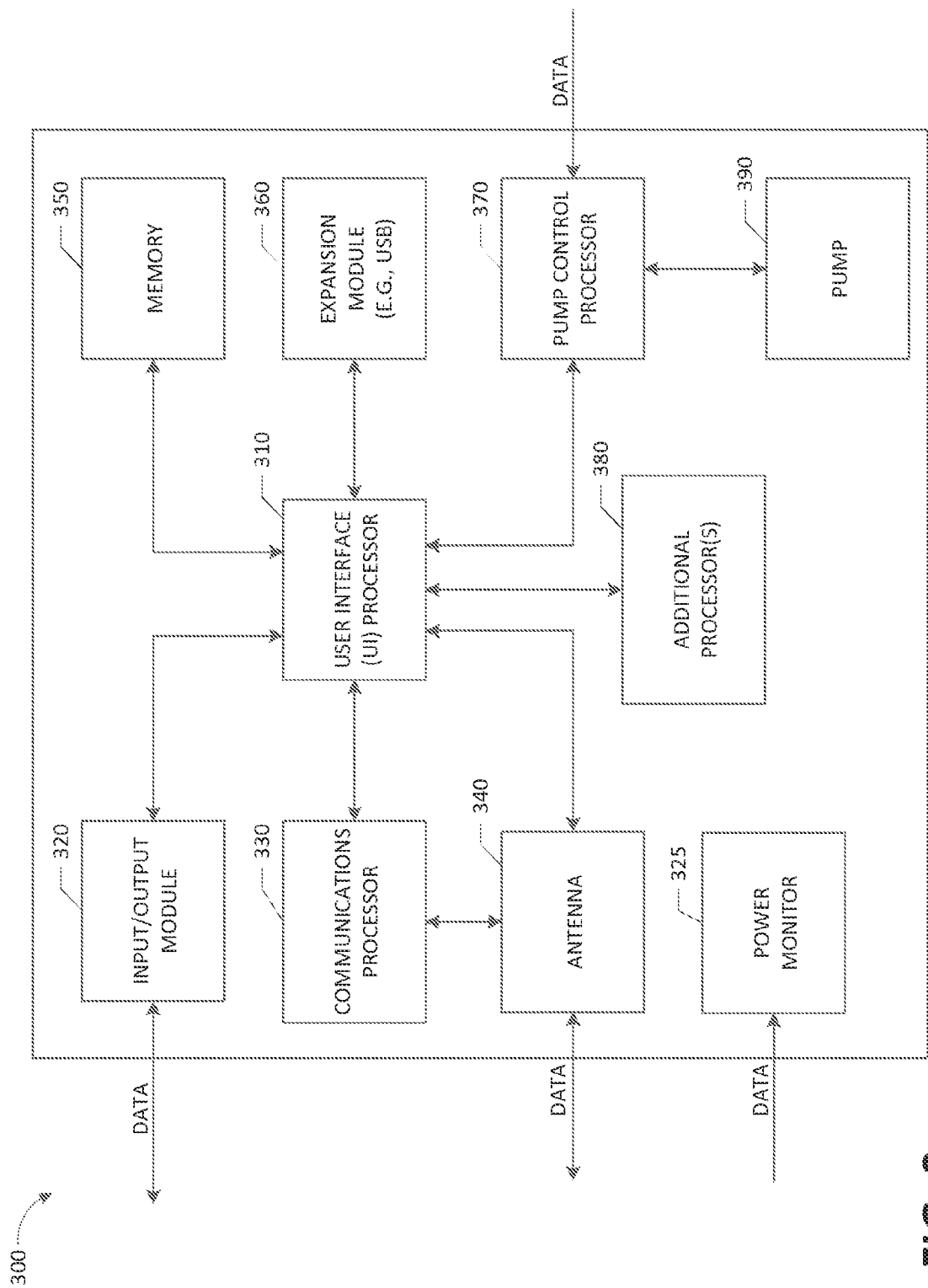
FIG. 3 illustrates an electrical component schematic of a pump assembly according to some embodiments.

FIG. 3 illustrates an electrical component schematic 300 of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors. It may be advantageous to utilize multiple processors in order to allocate or assign various tasks to different processors. A first processor can be responsible for user activity and a second processor can be responsible for controlling the pump. This way, the activity of controlling the pump, which may necessitate a higher level of responsiveness (corresponding to higher risk level), can be offloaded to a dedicated processor and, thereby, will not be interrupted by user interface tasks, which may take longer to complete because of interactions with the user.

The pump assembly can comprise a user interface processor or controller 310 configured to operate one or more components for accepting user input and providing output to the user, such as the display 206, buttons 212, etc. Input, to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal and/or external to the processor 310. Any suitable type of memory can be used, including volatile and/or non-volatile memory, such as RAM, ROM, magnetic memory, solid-state memory, Magnetoresistive random-access memory (MRAM), and the like.

The pump assembly can further comprise a power monitor 325 configured to determine data regarding the power source (such as a battery) of the pump assembly. The power monitor 325 can be configured to determine battery status based on data received from one or more hardware components, such as a battery gas gauge circuit. For example, the power monitor 325 can be configured to determine remaining battery capacity as a percentage of the total battery capacity based on data received from the battery gas gauge circuit. The power monitor 325 alone or in combination with one or more processors disclosed herein can also be configured to determine the remaining use time of the pump assembly. In some embodiments, this is performed by determining the current load conditions and dividing the current battery capacity by the current load conditions to determine the remaining use time. The current load conditions can be determined, for example, based on power used by the pump assembly at a point of time or over a period of time. For instance, current used by the pump assembly can be averaged over a period of time to obtain the current load conditions. As an example, suppose that the average current drawn over the pump assembly over one minute is X amperes, and that the remaining batter capacity is Y amperes. In this example, the remaining usage time is Y/X minutes.

In some embodiments, the power monitor 325 alone or in combination with one or more processors disclosed herein is configured to indicate or trigger a low battery alarm when it has been determined that the remaining usage time satisfies a low battery condition. For example, the low battery condition can be a certain duration of remaining usage time, such as 30 minutes, 1 hour, 2 hours, and the like. The power monitor 325 alone or in combination with one or more processors disclosed herein can also be configured to indicate or trigger a critical low battery alarm when it has been determined that the remaining usage time satisfies a critical low battery condition. For example, the critical battery condition can be a certain duration of remaining usage time, such a 5 minutes, 10 minutes, 20 minutes, 1 hour, and the like. The pump assembly can be configured to power off or shut down when it has been determined that the remaining usage time satisfies a battery depleted condition, which can be a certain duration of remaining usage time, such as 1 minute, 5 minutes, 10 minutes, 12 minutes, and the like. This way, a graceful shut down can be performed before the battery becomes fully depleted. Graceful shutdown can include stopping therapy, saving data, and the like.

In some embodiments, the power monitor 325 can be configured to determine, such as based on data received data from one or more hardware components, the charging status of the battery as well as whether a battery failure has occurred. The power monitor 325 can be configured to receive data from, for example, a battery charging circuit to determine whether the battery is actively charging. Further, the power monitor 325 can be configured to receive data from a battery gas gauge circuit to determine if there has been a battery failure. In some embodiments, the power monitor 325 can be configured to indicate or trigger a device technical failure alarm when it has determined that the battery has failed.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure pump 390. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump control processor 370 can measure pressure in a fluid flow path, using data received from one or more pressure sensors, calculate the rate of fluid flow, and control the pump. The pump control processor 370 can control pump motor so that a desired level of negative pressure is achieved in the wound cavity 110. The desired level of negative pressure can be pressure set or selected by the user. In various embodiments, the pump control processor 371 controls the pump (e.g., pump motor) using pulse-width modulation (PWM). A control signal for driving the pump can be a 0-100% duty cycle PWM signal. The pump control processor 370 can perform flow rate calculations and detect various conditions in a flow path. The pump control processor 370 can communicate information to the processor 310. The pump control processor 370 can include internal memory and/or can utilize memory 350. The pump control processor 370 can be a low-power processor.

A communications processor 330 can be configured to provide wired and/or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), WiFi connectivity. Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. The communications processor 330 can provide dual GPS/cellular functionality. Cellular functionality can, for example, be 3G functionality. In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. The pump assembly can include a SIM card, and SIM-based positional information can be obtained.

The communications processor 330 can communicate information to the processor 310. The communications processor 330 can include internal memory and/or can utilize memory 350. The communications processor 330 can be a low-power processor.

In some embodiments, the pump assembly can track and store various data, such as one or more of positioning data, therapy parameters, logs, device data, and so on. The pump assembly can track and log therapy and other operational data. Data can be stored, for example, in the memory 350.

In some embodiments, using the connectivity provided by the communications processor 330, the device can upload any of the data stored, maintained, and/or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. The pump assembly can provide Internet browsing functionality using one or more browser programs, mail programs, application software (e.g., apps), etc.

In some embodiments, the communications processor 330 can use the antenna 340 to communicate a location of the pump assembly, such as a location of a housing of the pump assembly, to other devices in the proximity (for example, within 10, 20, or 50 meters and the like) of the pump assembly. The communications processor 330 can perform one-way or two-way communication with the other devices depending on the implementation. The communications transmitted by the communications processor 330 can include identifying information to uniquely identify the pump assembly relative to one or more other pump assemblies also in the proximity of the pump assembly. For example, identifying information can include a serial number or a value derived from the serial number. The signal strength of the transmitted communications by the communications processor 330 can be controlled (for example, maintained at a constant or substantially constant level) to enable another device to determine a distance to the pump assembly, such as a distance between the device and the pump assembly.

In some embodiments, the communications processor 330 can communicate with other devices in the proximity of the pump assembly so that the communications processor 330 can itself determine a distance from the pump assembly to the other devices. The communications processor 330, in such embodiments, can track and store the distance from the pump assembly to the other devices or indications of change in the distance over time, and the communications processor 330 can later provide this information to the other devices. For instance, the communications processor 330 can determine a duration of time during which the pump assembly has been removed from a coverage area of a device and subsequently report this time to the device upon being returned to the coverage area.

Figure 4:
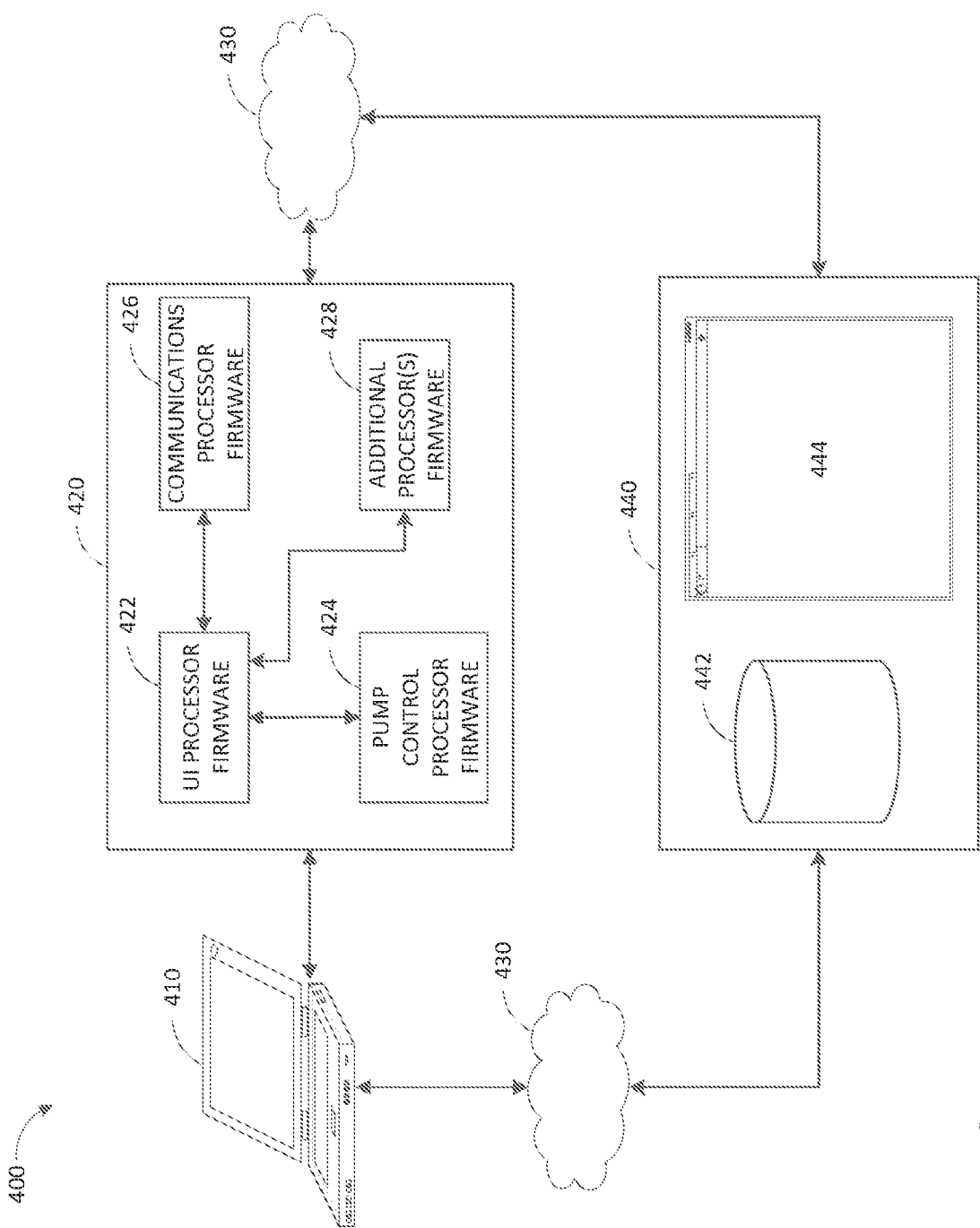
FIG. 4 illustrates a firmware and/or software diagram according to some embodiments.

FIG. 4 illustrates a firmware and/or software diagram 400 according to some embodiments. A pump assembly 420 includes a user interface processor firmware and/or software 422, which can be executed by the user interface processor 310, pump control processor firmware and/or software 424, which can be executed by the pump control processor 370, communications processor firmware and/or software 426, which can be executed by the communications processor 330, and additional processor(s) firmware and/or software 428, which can be executed by one or more additional processors 380. The pump assembly 420 can be connected to a computer 410, which can be a laptop, desktop, tablet, smartphone, and the like. A wired or wireless connection can be utilized to connect the computer 410 to the pump assembly 420. For example, a USB connection can be used. The connection between the computer 410 and the pump assembly 420 can be used for various activities, such as pump assembly location tracking, asset tracking, compliance monitoring, selection, uploading of logs, alarms, and other operational data, and adjustment of therapy settings, upgrading of software and/or firmware, and the like. The pump assembly 420 and computer 410 can communicate with a remote computer or server 440 via the cloud 430. The remote computer 440 can include a data storage module 442 and a web interface 444 for accessing the remote computer.

The connection between the computer 410 and pump assembly 420 can be utilized to perform one or more of the following: initialization and programming of the pump assembly 420, firmware and/or software upgrades, maintenance and troubleshooting, selecting and adjusting therapy parameters, and the like. In some embodiments, the computer 410 can execute an application program for communicating the pump assembly 420.

In some embodiments, the pump assembly 420 keeps track of a maintenance schedule and provides an indication (such as message, indicator, or alarm screen as described below) when maintenance is due or past due. For example, maintenance can be performed once a year, and the pump assembly 420 can provide an indication when a year from the last performed maintenance has elapsed. This indication can be provided when the pump assembly boots up or at any other suitable time. Information on duration of time before next maintenance is due can also be provided, for example, on the user interface under device information menu (see FIG. 5E).

The pump assembly 420 can upload various data to the remote computer (or multiple remote computers) 440 via the cloud 430. As explained above, upload data can include activity log(s), alarm log(s), therapy duration information, total therapy time, lifetime therapy information, device information, device location information, patient information, etc. In addition, the pump assembly 420 can receive and process commands received from the cloud 430.

Operation of the Pump Assembly

In some embodiments, the pump assembly 230 can be operated using a touchscreen interface displayed on the screen 206. Various graphical user interface (GUI) screens present information on systems settings and operations, among other things. The touchscreen interface can be actuated or operated by a finger (or a stylus or another suitable device). Tapping a touchscreen cam result in making a selection. To scroll, a user can touch screen and hold and drag to view the selections. Additional or alternative ways to operate the touchscreen interface can be implemented, such as multiple finger swipes for scrolling, multiple finger pinch for zooming, and the like.

FIGS. 5A-5I illustrate graphical user interface screens according to some embodiments. The GUI screens can be displayed on the screen 206, which can be configured as a touchscreen interface. Information displayed on the screens can be generated based on input received from the user. The GUI screens can be utilized for initializing the device, selecting and adjusting therapy settings, monitoring device operation, uploading data to the network (e.g., cloud), and the like. The illustrated GUI screens can be generated directly by an operating system running on the processor 310 and/or by a graphical user interface layer or component running on the operating system. For instance, the screens can be developed using Qt framework available from Digia.

Figure 5A:
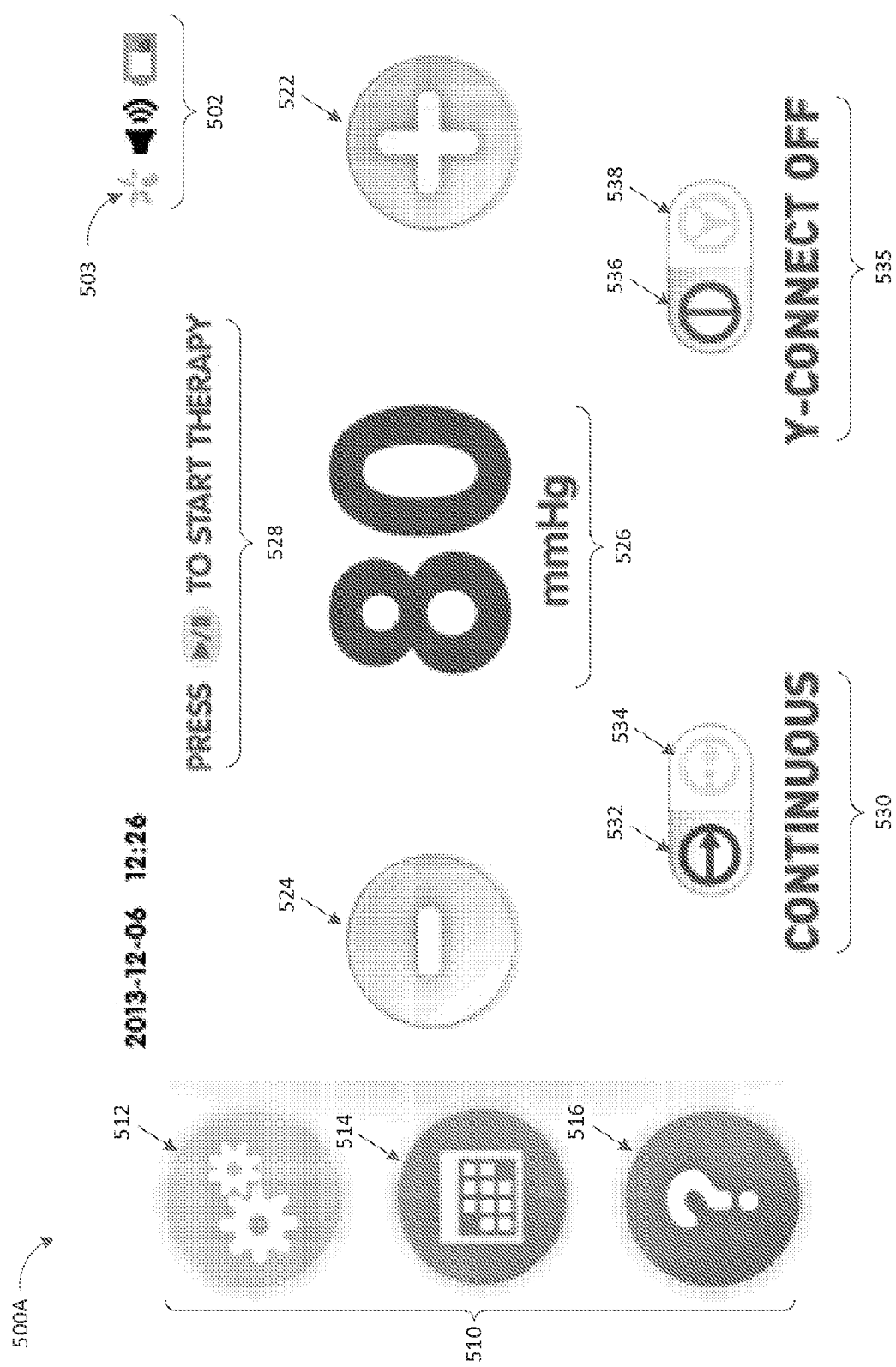

FIG. 5A illustrates a therapy settings screen 500A according to some embodiments. The therapy settings screen 500A can be displayed after the pump assembly has been initialized (e.g., screen 500A can function as a home screen). The therapy settings screen 500A includes a status bar 502 that comprises icons indicating operational parameters of the device. Animated icon 503 is a therapy delivery indicator. When therapy is not being delivered, icon 503 can be static and displayed in a color, such as gray. When therapy is being delivered, icon 503 can turn a different color, such as orange, and becomes animated, such as, rotates, pulsates, become filled with color (see FIG. 5C), etc. Other status bar icons include a volume indicator and a battery indicator, and may include additional icons, such as wireless connectivity. The therapy settings screen 500A includes date/time and information. The therapy settings screen 500A includes a menu 510 that comprises menu items 512 for accessing device settings, 514 for accessing logs, 516 for accessing help, and 518 (see, for example, FIGS. 5C and 5E) for returning to the therapy settings screen (or home screen) from other screens. The pump assembly can be configured so that after a period of inactivity, such as not receiving input from the user, therapy settings screen 500A (or home screen) is displayed. Additional or alternative controls, indicators, messages, icons, and the like can be used.

The therapy settings screen 500A includes negative pressure up and down controls 522 and 524. Up and down controls 522 and 524 can be configured to adjust the negative pressure setpoint by a suitable step size, such as ±5 mmHg. As is indicated by label 526, the current therapy selection is −80 mmHg (or 80 mmHg below atmospheric pressure). The therapy settings screen 500A includes continuous/intermittent therapy selection 530. Continuous therapy selection screen can be accessed via control 532 and intermittent therapy selection screen can be accessed via control 534. As is illustrated, the current therapy setting is to continuously deliver negative pressure at −80 mmHg. As is indicated by message 528, therapy delivery can be initiated by pressing a button, such as button 212b on the pump assembly 230. The therapy settings screen 500A includes Y-connector selection 535 for treating multiple wounds, such as two, three, etc. wounds, with one pump assembly 230. Control 536 selects treatment of a single wound, and control 538 selects treatment of more than one wound by the pump assembly. As is indicated by the label "Y-CONNECT OFF," the current selection is to treat a single wound. Additional or alternative controls, indicators, messages, icons, and the like can be used.

Figure 5B:
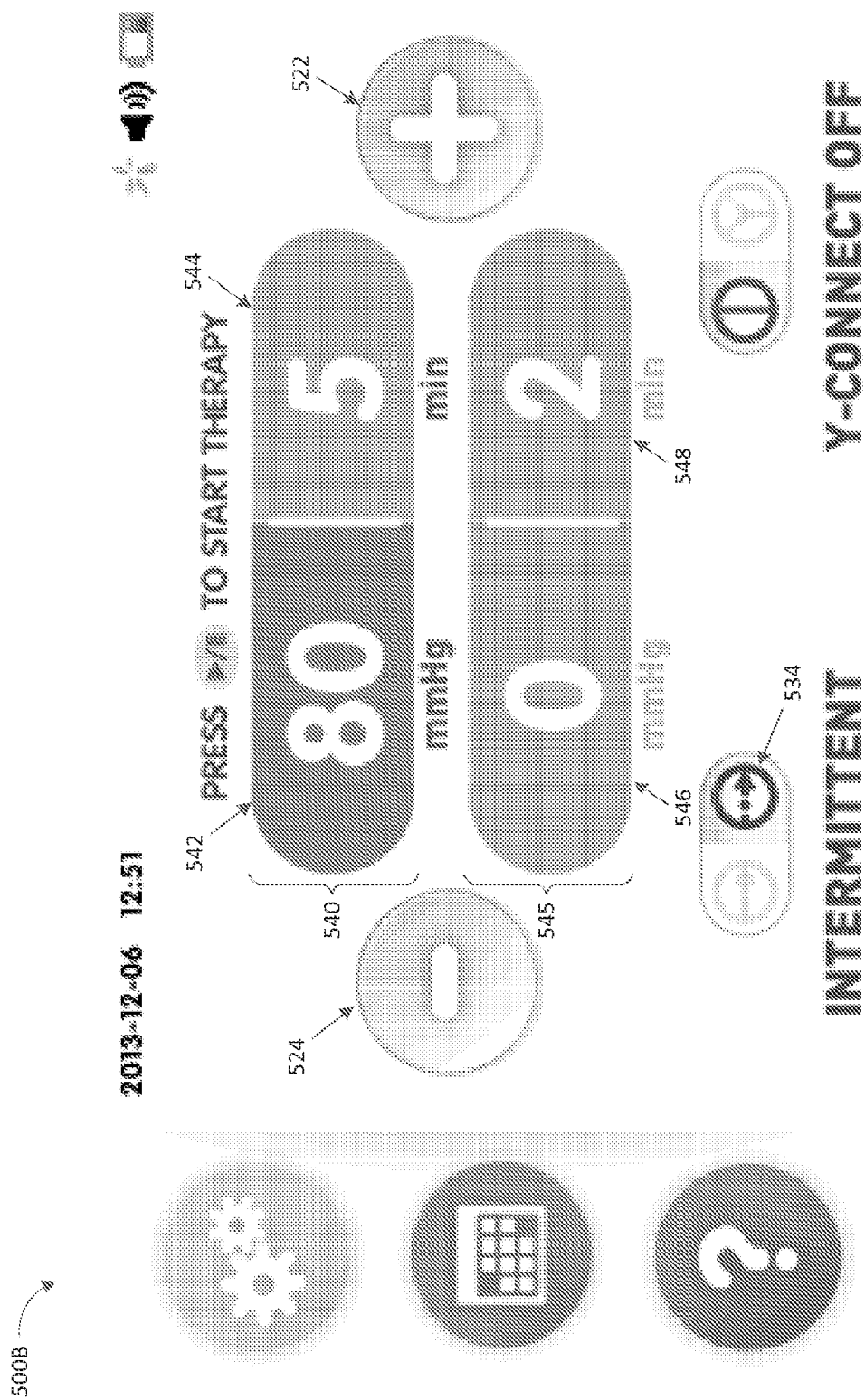

FIG. 5B illustrates therapy settings screen 500B for delivering intermittent therapy according to some embodiments. Screen 500C can be accessed via control 534. Therapy settings screen 500B includes intermittent therapy settings 540 and 545. As is illustrated by settings of controls 542, 544, 546, and 548, respectively, current therapy selection is applying −80 mmHg of reduced pressure for 5 minutes followed by 2 minutes of applying atmospheric pressure (or turning off the vacuum pump). Such treatment cycles can be repeated until stopped by the user or by the pump assembly 230. Negative pressure levels and time durations can be adjusted by selecting one or more of controls 542, 544, 546, and 548 and operating the up or down controls 522 or 524 until desired values are selected. In some implementations, more than two negative pressure values and corresponding durations can be selected for treatment of a wound. For example, a user can select three or more negative pressure values and corresponding durations. Additional or alternative controls, indicators, messages, icons, and the like can be used.

Figure 5C:
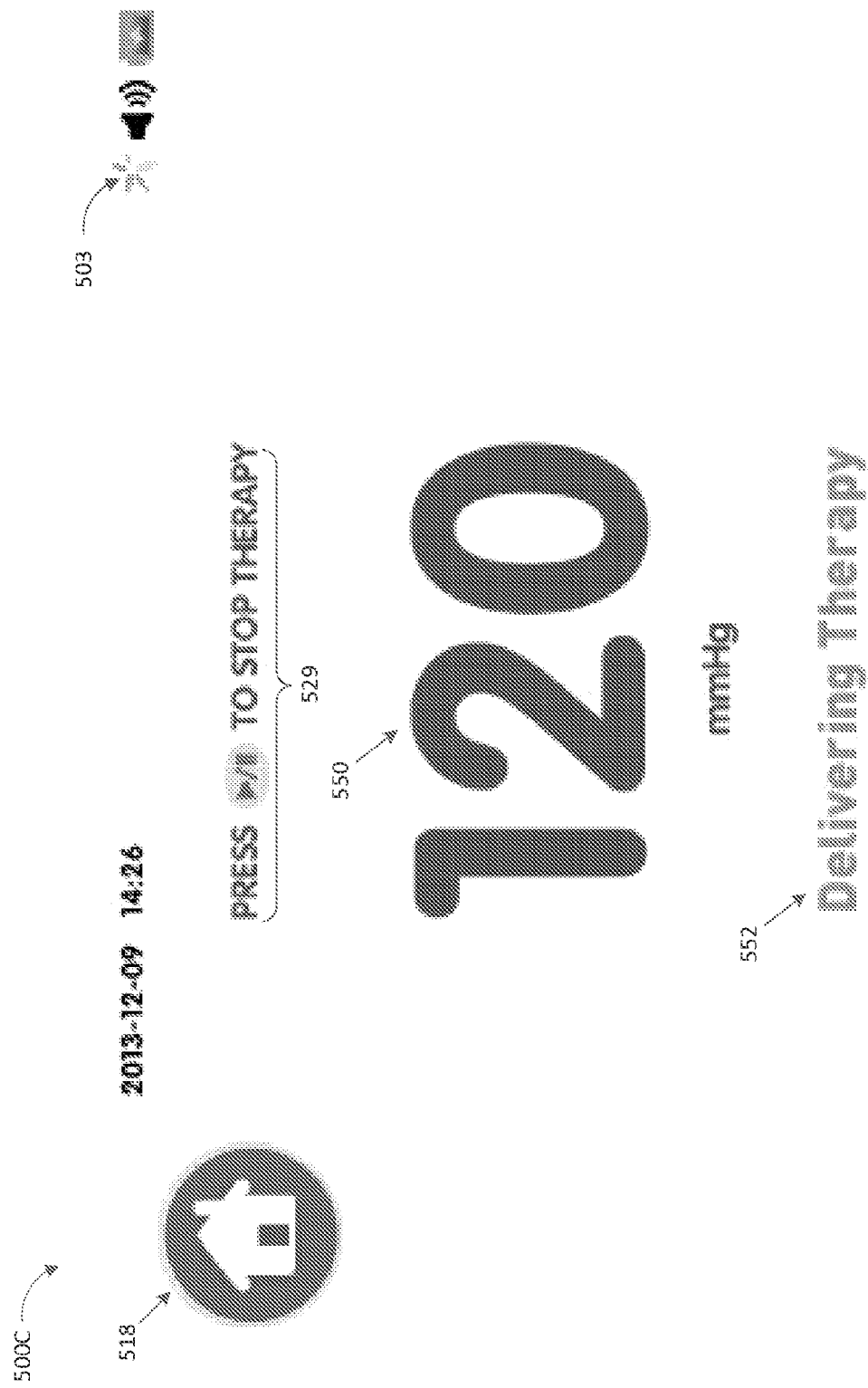
Figure 5D:
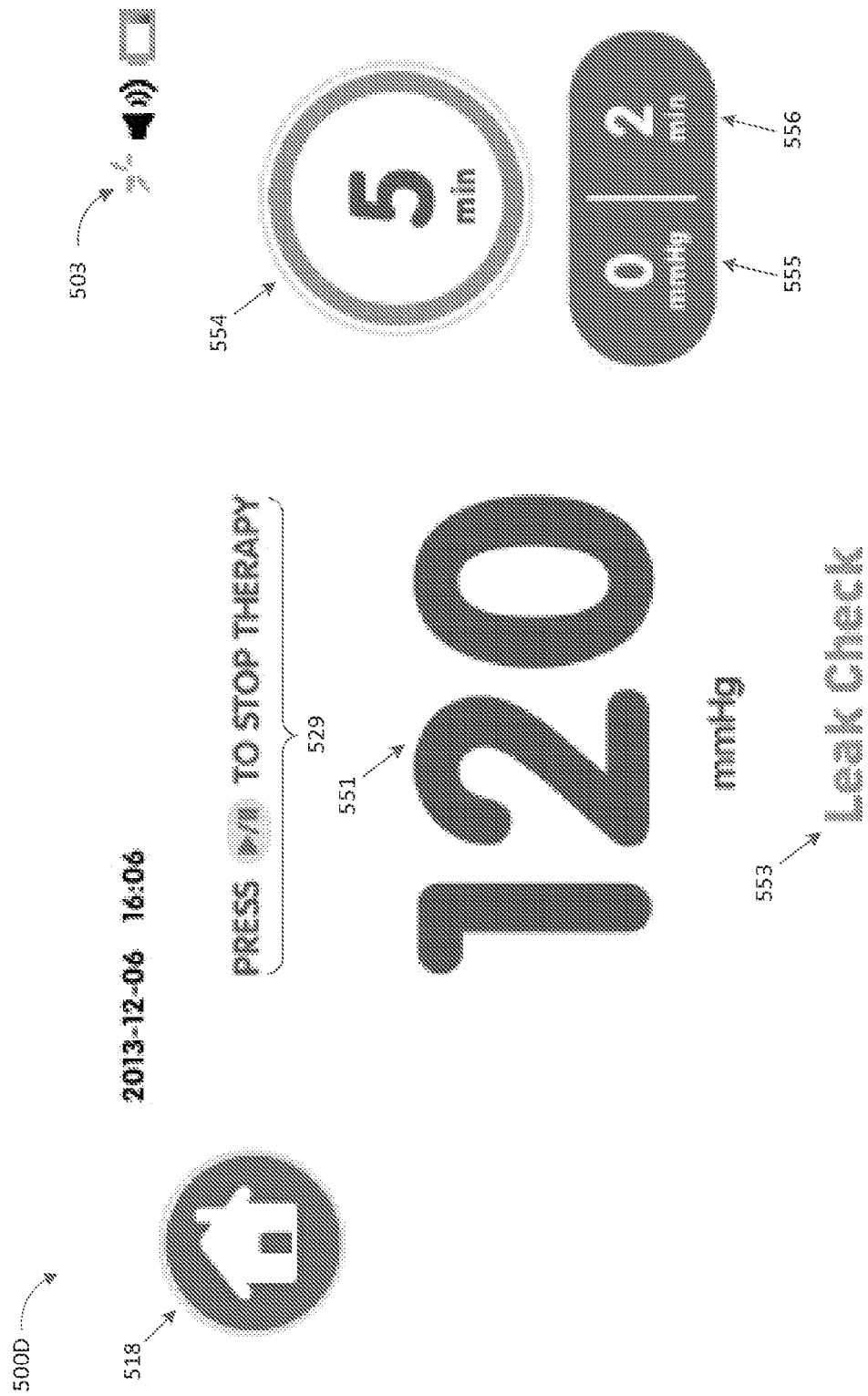

FIG. 5C illustrates therapy delivery screen 500C according to some embodiments. Screen 500C can be accessed by selecting desired therapy settings on the screen 500A or 500B and initiating therapy, such as by pressing the button 212b. As is illustrated, label 552 ("Delivering Therapy") indicates that continuous therapy at −120 mmHg of reduced pressure (label 560) is being delivered to a wound. Animated icon 503 indicates that therapy is being delivered by cycling though an animation. As is illustrated in FIGS. 5C and 5D, icon 503 is an energy burst having multiple petals, and the animation sequences through the petals becoming filled with orange color. Any other suitable animation or combination of animations can be used. Message 529 indicates that therapy settings can be stopped or paused by pressing a button, such as button 212b, on the pump assembly 230. Menu item 518 can be configured to return to the therapy settings screen (or home screen) 500A. Additional or alternative controls, indicators, messages, icons, and the like can be used.

FIG. 5D illustrates therapy delivery screen 500D according to some embodiments. Screen 500D can be displayed after the user has selected desired therapy settings on the screen 500B and has initiated therapy, such as by pressing button the 212b. As is illustrated, intermittent therapy is being delivered to a wound. Label 551 and tinier 554, respectively, indicate that negative pressure of −120 mmHg is being delivered to the wound for 5 minutes. Timer 554 can be configured to show the remaining amount of time, for example, as a number (e.g., "5 min"), as a relative amount (e.g., by adjusting the fill of the circle), and a combination of the two. Labels 555 and 556, respectively, indicate that 0 mmHg (or atmospheric pressure) is scheduled to be delivered to the wound for duration of 2 minutes upon expiration of the time period (e.g., 5 minutes) for delivering the first amount of negative pressure (e.g., −120 mmHg). Message 553 ("Leak Check") indicates that the pump assembly 230 is performing a leak check. As is further explained below, the pump assembly 230 can perform a leak check when it initiates delivery of negative pressure therapy to determine if the fluid flow path is sufficiently free of leaks (e.g., is properly sealed). Once it has been determined that no significant leaks are present, message 553 can indicate this fact to the user, such as by displaying the message "Seal Achieved." Menu item 518 can be configured to return to the therapy settings screen (or home screen). Additional or alternative controls, indicators, messages, icons, and the like can be used.

Figure 5E:
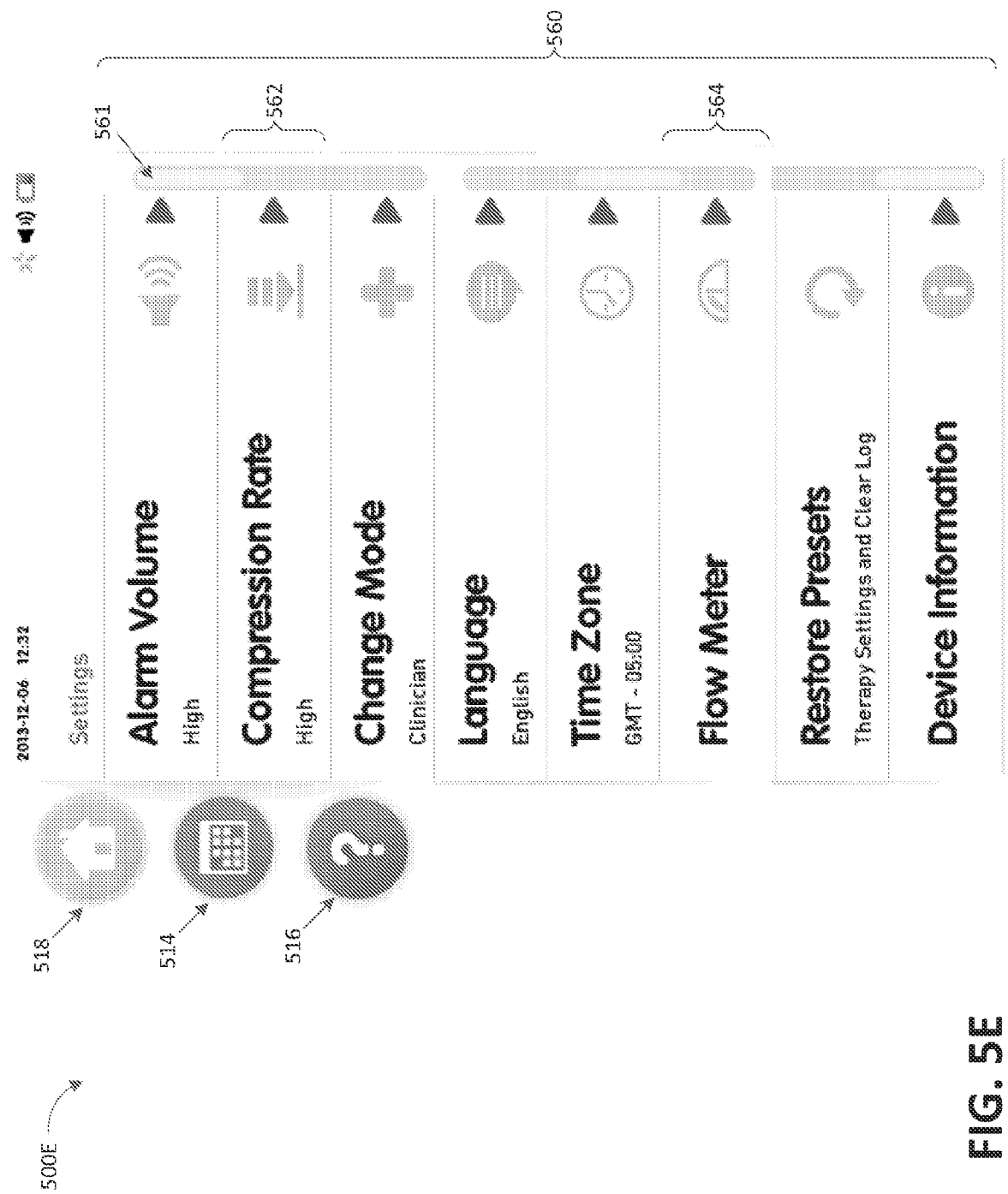

FIG. 5E illustrates settings screen 500E according to some embodiments. The settings screen 500E can be accessed by selecting menu item 512 (e.g., from screen 500A or 500B). As is illustrated, settings screen 500E includes a menu 560 for adjusting various operational parameters of the pump assembly 230, including alarm volume setting, compression setting 562, user mode setting (e.g., clinician or patient), language setting, time zone setting, flow meter 564, restore presets (e.g., factory presets), and device information. Attempting to set the user mode as clinician mode may prompt the user to enter a password or satisfy any other suitable security check. Operating the pump assembly in clinician mode can provide unrestricted access to all features and settings, whereas operating the pump assembly in patient mode can prevent inadvertent changes to therapy settings by preventing access to one or more features and settings, such as therapy settings, compression settings, and the like. Alternative or additional menu items can be displayed. The illustrated menu 560 is an expanded version of the menu showing all menu items. In use, menu 560 may only partially fit on the screen, and the menu items can be accessed via the scroll bar 561 or via any other suitable alternative or additional controls. Additional or alternative controls, indicators, messages, icons, and the like can be used.

Figure 5F:
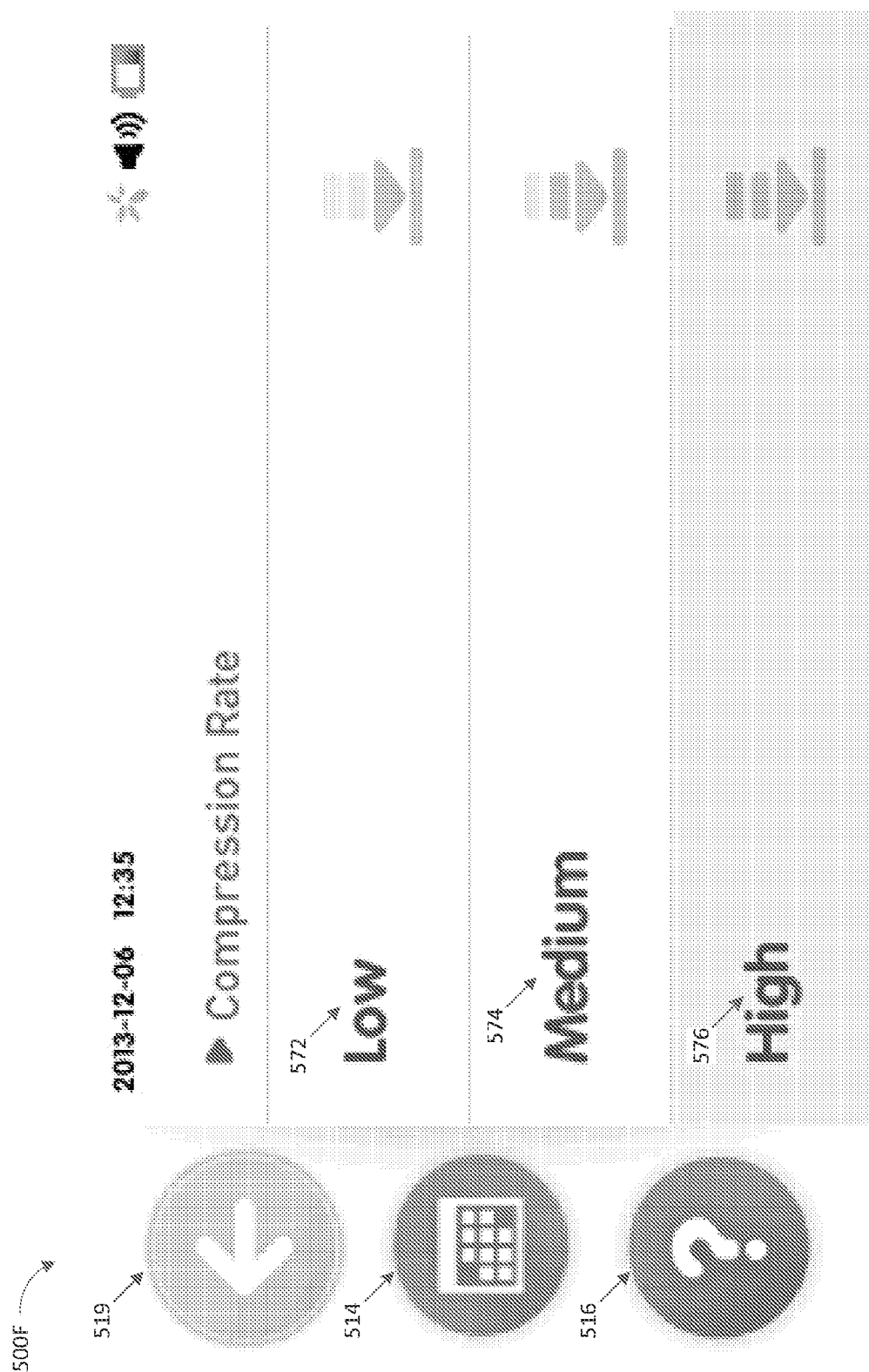

FIG. 5F illustrates compression settings screen 500F according to some embodiments. The screen 500F can be accessed by selecting the menu item 562. The screen 500F includes three compression settings selections: low 572, medium 574, and high 576. As is explained below, these selections control the time it takes to reach a desired or set vacuum level at the wound so that the change in vacuum pressure is gradual. Compression may be defined as the maximum change (either increase or decrease) in negative pressure per unit time. For example, selecting a high compression 576 will result in the most rapid achievement of more negative or more positive pressure under the dressing. Menu item 519 can be configured to return to the settings screen 500E. In certain embodiments, compression settings screen 500E may be accessed only if clinician mode has been previously selected. A clinician may select appropriate compression setting based on one or more physiological parameters, such as wound type, patient's age, physical condition, etc. Additional compression settings, such as very low, very high, and the like can be provided. Additional or alternative controls, indicators, messages, icons, and the like can be used.

Figure 5G:
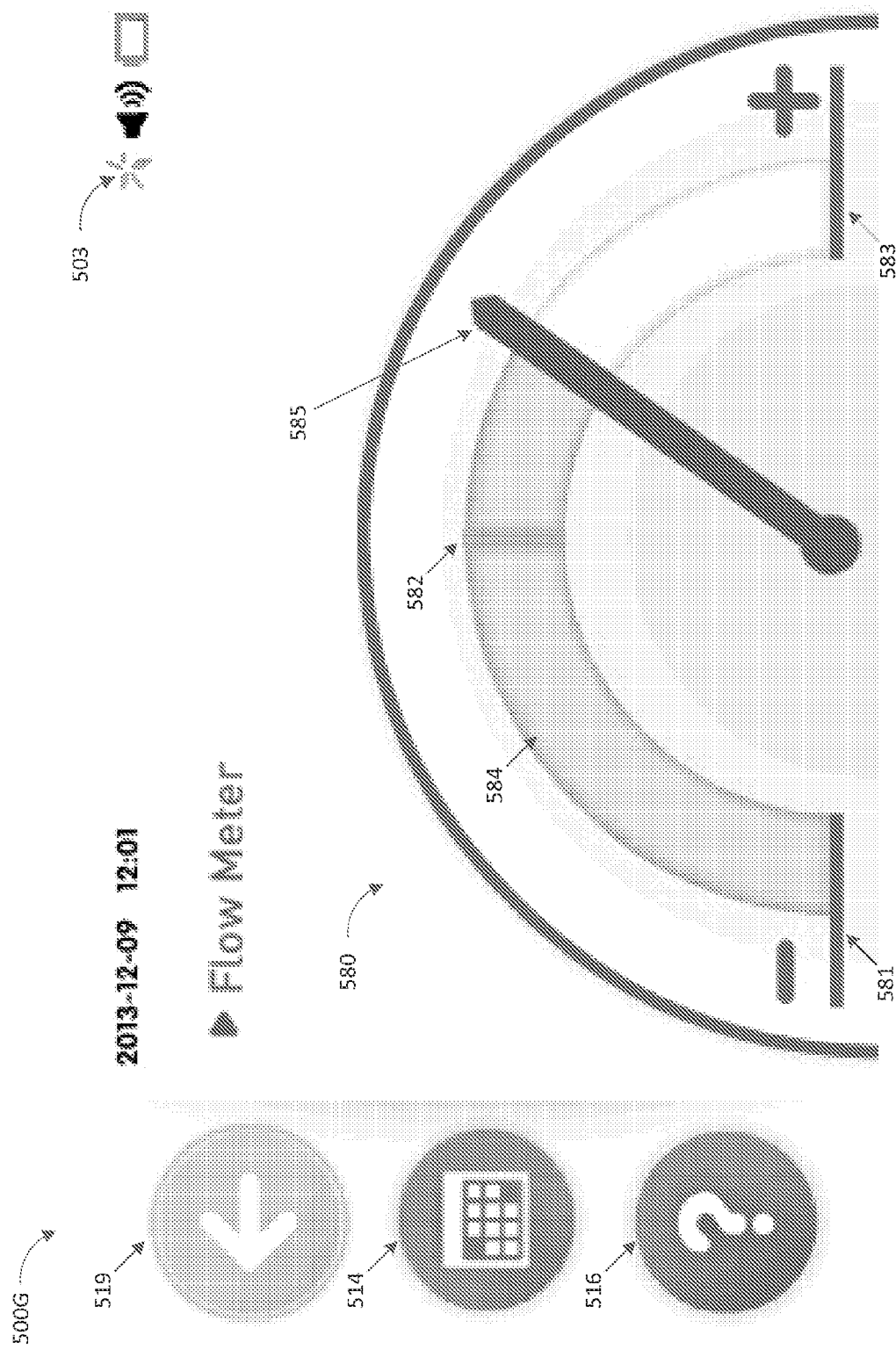
Figure 51:
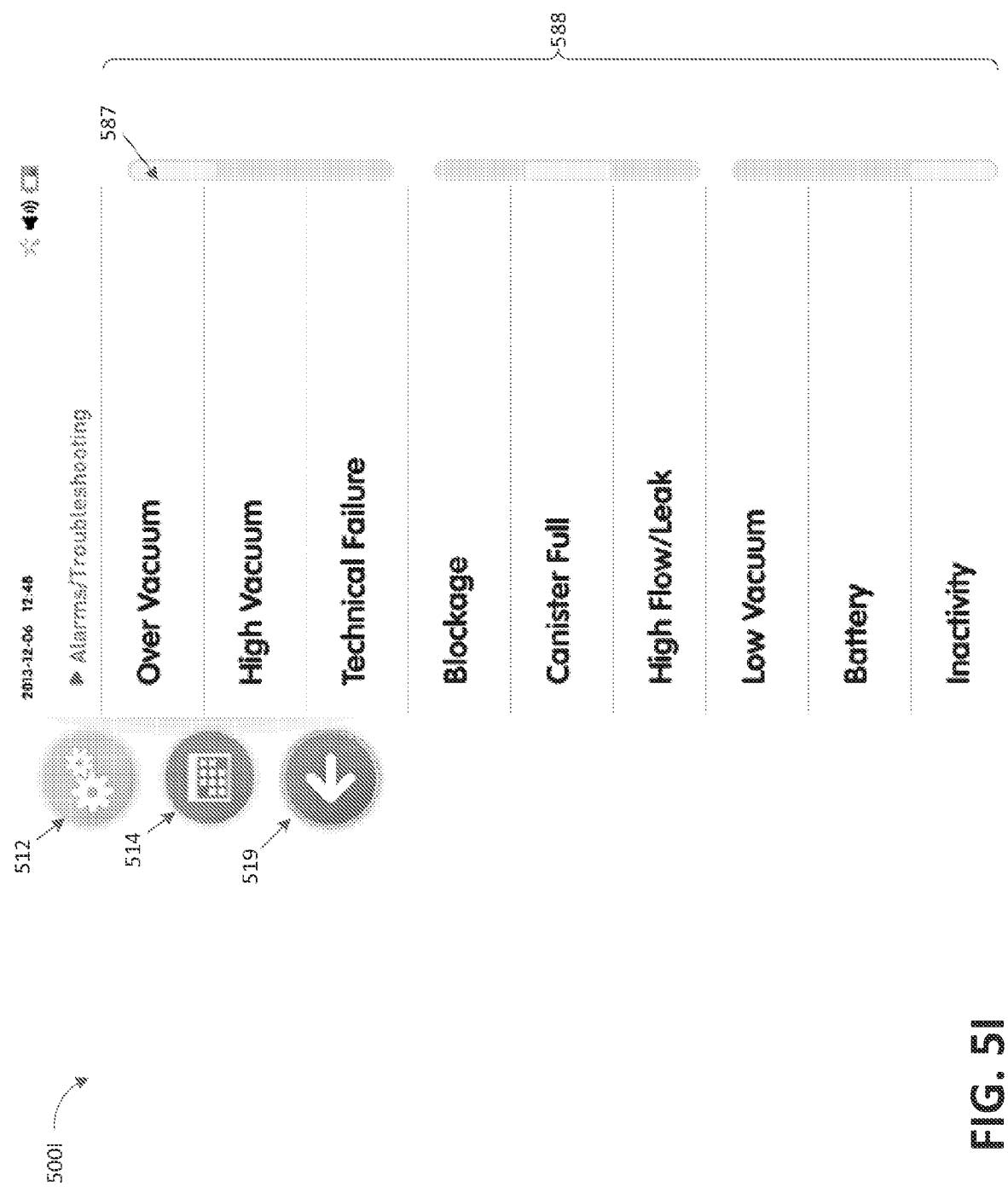

FIG. 5G illustrates flow meter screen 500C according to some embodiments. The screen 500G can be accessed by selecting the menu item 564 in FIG. 5E. The screen 500G can visually depict the determined or calculated rate of air (or gas) flow in the fluid flow path, which can include the therapy unit assembly, wound dressing, and tubing connecting the therapy unit assembly to the wound dressing. The screen 500G illustrates a gauge 580 that visually depicts the determined flow rate and can be used for detection of one or more leaks in the fluid flow path. Other controls for depicting the flow rate can be alternatively or additionally used, such as horizontal or vertical bars, digital gauges, labels, and the like.

As is illustrated, the gauge 580 includes a dial 584 with markings 581 indicating absence of leaks or a very small leak (positioned at the beginning of the dial), 582 indicating medium leak (positioned at the middle of the dial), and 583 indicating high leak (positioned at the end of the dial). The gauge 580 also includes a needle 585 that indicates the determined leak rate on the dial 584. The dial 584 can be configured to be filled in various colors that visually indicate the leak rate. For example, green color can indicate a low level leak, yellow color can indicate a higher level (or significant) leak, and red color can indicate a leak of a high level. As is depicted by the position of the needle 585 being between the marking 582 (middle of the dial) and 583 (end or maximum setting of the dial), a fairly severe leak has been detected. The gauge 580 can assist a user in locating leaks. Other controls for depicting the leak rate can be alternatively or additionally used, such as horizontal or vertical bars, digital gauges, labels, and the like.

FIG. 5H illustrates flow meter screen 500H according to some embodiments. In contrast with the screen 500G, screen 500H illustrates a lower detected leak. This is depicted by the needle 585 being positioned closer to the marking 581 (e.g., needle 585 is to the left of marking 582). In some embodiments, detection of leaks exceeding a certain threshold may trigger an alarm. That is, in the event of a low vacuum level at the wound (e.g., due to high leak), the flow meter screen 500C can be displayed to help locate the leak (or leaks) in the fluid flow path. Flow meter screen 500G or 500H can be displayed while therapy is being delivered by the pump assembly, as is illustrated by the animated icon 503.

FIG. 5I illustrates alarms and troubleshooting screen 500I according to some embodiments. The screen 500I can be accessed by selecting the menu item 516 for accessing help (see FIG. 5E) and selecting alarms menu item from the help screen (not shown). As is illustrated, screen 500I includes a menu 588 with menu items for various alarm and troubleshooting categories, including over vacuum, high vacuum, blockage, canister flow, high flow/leak, and low or insufficient vacuum (as explained below) as well as technical failure (e.g., unrecoverable error), battery (e.g., low battery, critical low battery, battery failed), and inactivity (e.g., pump assembly is powered on an has been left without user interaction for longer than a certain period of time, such as 15 minutes). Alternative or additional menu items can be displayed. Accessing a particular menu item can bring up a screen with step-by-step instructions to assist in resolving the corresponding alarm. The instructions can include a combination of text, audio, video, etc. The illustrated menu 588 is an expanded version of the menu showing all menu items. In use, menu 588 may only partially fit on the screen, and menu items can be accessed via the scroll bar 587 or via any other suitable alternative or additional controls. Additional or alternative controls, indicators, messages, icons, and the like can be used.

FIGS. 6A-6G illustrate alarm screens according to some embodiments. The illustrated screens can be displayed in response to a condition or set of conditions detected by the pump assembly in order to alert the user. In the event of an alarm, for example, the therapy unit can perform one or more of the following: sound an audible alarm, display an alarm screen, illuminate the indicator 204 in a specific color, such as yellow. The therapy unit can be configured to stop or suspend delivering therapy in the occurrence of an over vacuum or high vacuum alarm. If occurrence of other alarms is detected, the therapy unit can continue delivery of therapy.

In some embodiments, the therapy unit can be configured to continuously monitor for or check for one or more conditions that may trigger an alarm. However, as explained further below, the therapy can be further configured to suspend detection of some or all of the conditions and suppress one or more alarm during certain states associated with delivery of negative pressure.

Figure 6A:
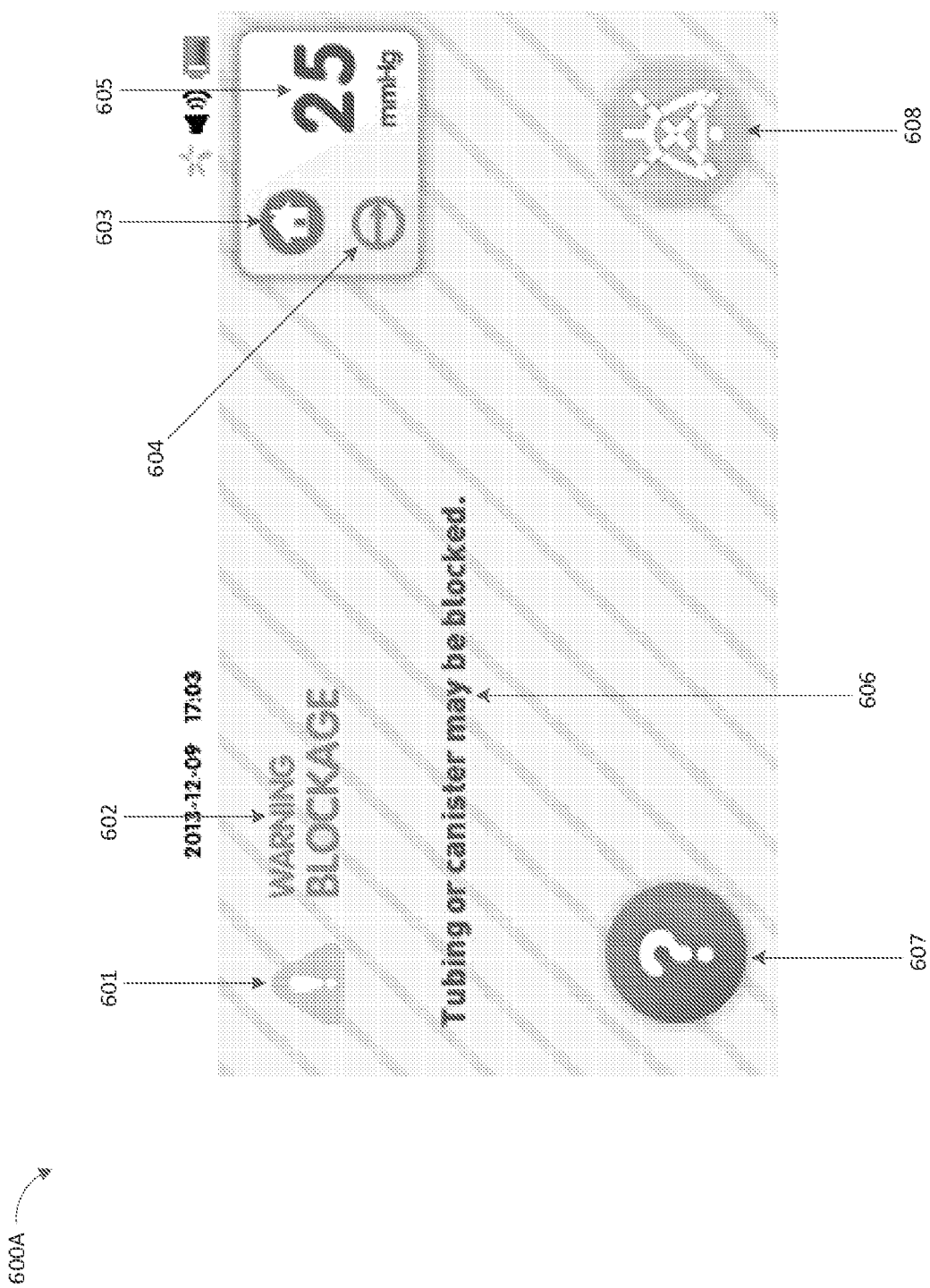
FIGS. 6A-6G illustrate alarms screens according to some embodiments.

FIG. 6A illustrates a blockage alarm screen 600A according to some embodiments. Indicator 601 indicates alarm condition. Label 602 is a description of the alarm (e.g., "WARNING BLOCKAGE"). Icon 603 is configured to return the home screen, such as screen 500A. Labels 604 and 605 respectively provide information about current therapy settings. As is illustrated, continuous therapy at −25 mmHg of reduced pressure is being applied to a wound. Label 606 provides suggested action to correct the alarm (e.g., "Tubing or canister may be blocked"). Icon 607 is configured to bring up alarms and troubleshooting screen 500I in case the user desires more detailed information regarding the alarms and troubleshooting. Icon 608 is configured to silence the alarm permanently or temporarily. For some alarms, such as non-critical alarms, audible tones can be temporarily silenced by selecting icon 608. If the audible alarm has been temporarily silenced and a new alarm occurs, the audible alarm for the new alarm may sound and the new alarm may be displayed. When multiple alarm messages are present, the therapy assembly can alternate between the alarm screens.

Figure 6B:
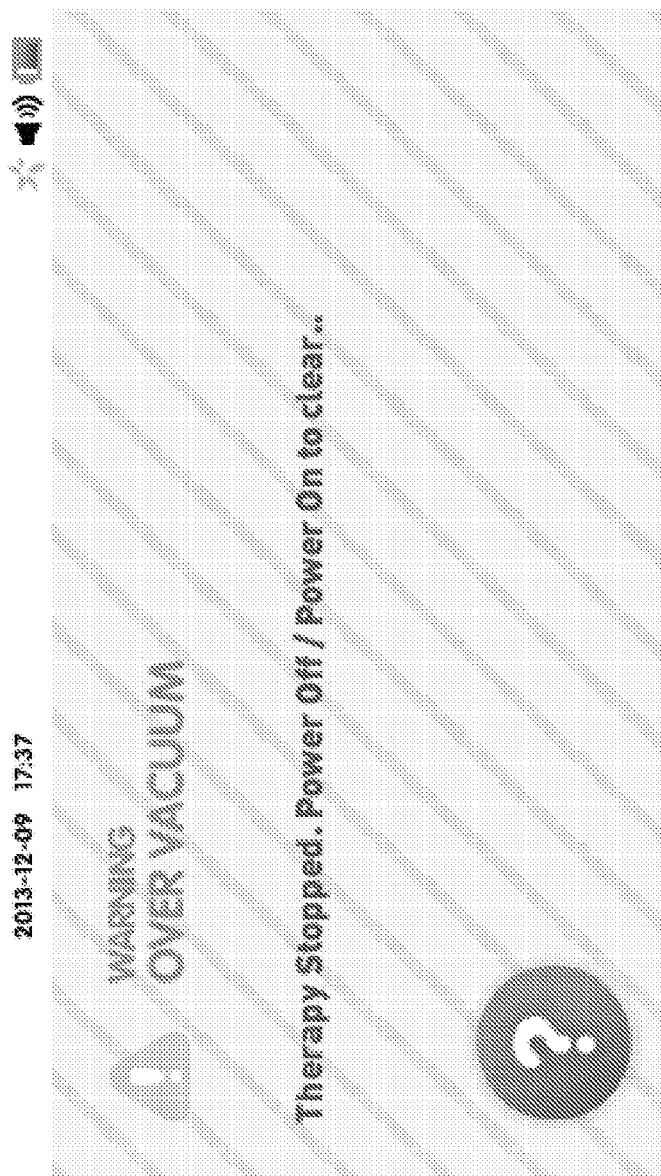

Blockage alarm screen 600A can indicate detection of a blockage in the flow path, such as in a conduit connecting the canister (or pump in a canisterless system) with the wound dressing. The alarm may be resolved by clearing the blockage. The pump assembly may continue to attempt to provide desired therapy to the wound after blockage has been detected. FIG. 6B illustrates an over vacuum alarm screen 600B according to some embodiments. As is illustrated, the description of the alarm is "OVER VACUUM," and suggested action to correct the alarm is "Power Off/Power On to clear." This alarm screen can indicate that the therapy unit has detected an excessively high vacuum in the fluid flow path (e.g., exceeding −235 mmHg or any other suitable value), potentially due to device malfunction. The pump assembly can be configured to stop or suspend delivering therapy until the over vacuum condition has been corrected. An audible alarm can be generated, which may not be paused (hence the icon 608 is not displayed in the screen 600B). As suggested, the alarm may be resolved by power cycling the pump assembly.

Figure 6C:
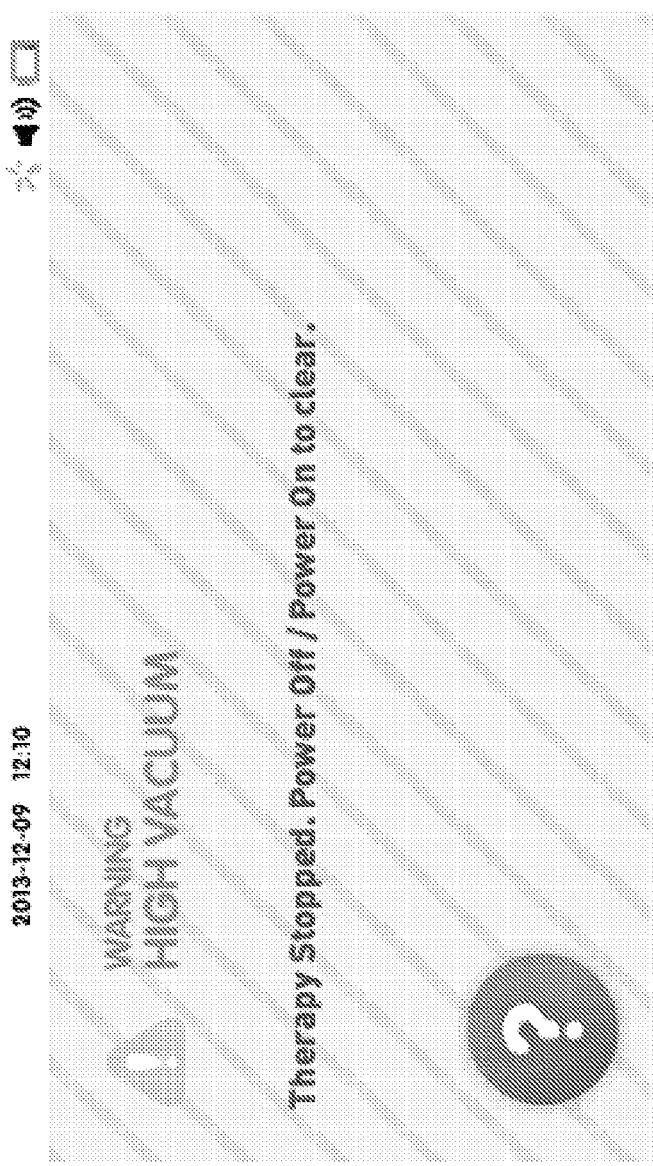

FIG. 6C illustrates a high vacuum alarm screen 600C according to some embodiments. As is illustrated, the description of the alarm is "HIGH VACUUM," and suggested action to correct the alarm is "Power Off/Power On to clear." This alarm screen can indicate that the therapy unit has detected a high vacuum condition (e.g., exceeding −15 mmHg above the therapy setpoint or any other suitable value), potentially due to a blockage or device malfunction. The pump assembly can be configured to stop or suspend delivering therapy until the high vacuum condition has been corrected. An audible alarm can be generated, which may not be paused (hence the icon 608 is not displayed in the screen 600C). As suggested, the alarm may be resolved by power cycling the pump assembly.

Figure 6D:
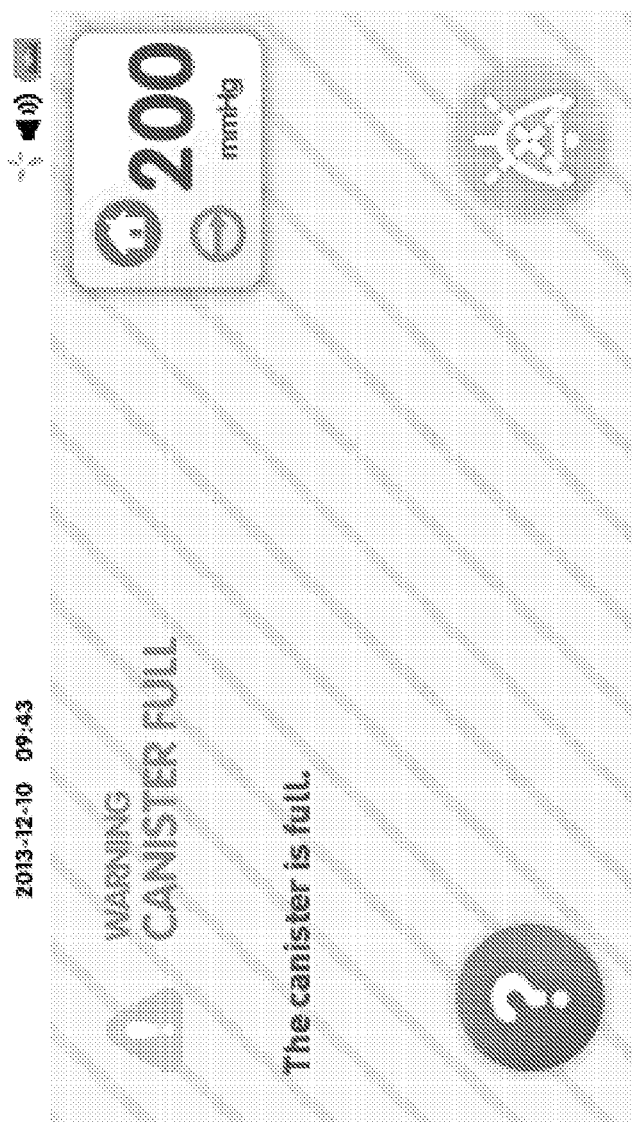

FIG. 6D illustrates a canister full alarm screen 600D according to some embodiments. As is illustrated, the description of the alarm is "CANISTER FULL" because it has been detected that the canister is full or the internal canister filter is covered with fluid. The alarm may be resolved by replacing the canister. The pump assembly may continue to attempt to provide desired therapy to the wound. The alarm may be silenced. In some systems, such as in canisterless systems where a dressing is configured to absorb fluid removed from the wound, dressing full condition or dressing filter occluded condition can be detected and indicated in a manner similar to the canister full condition.

Figure 6E:
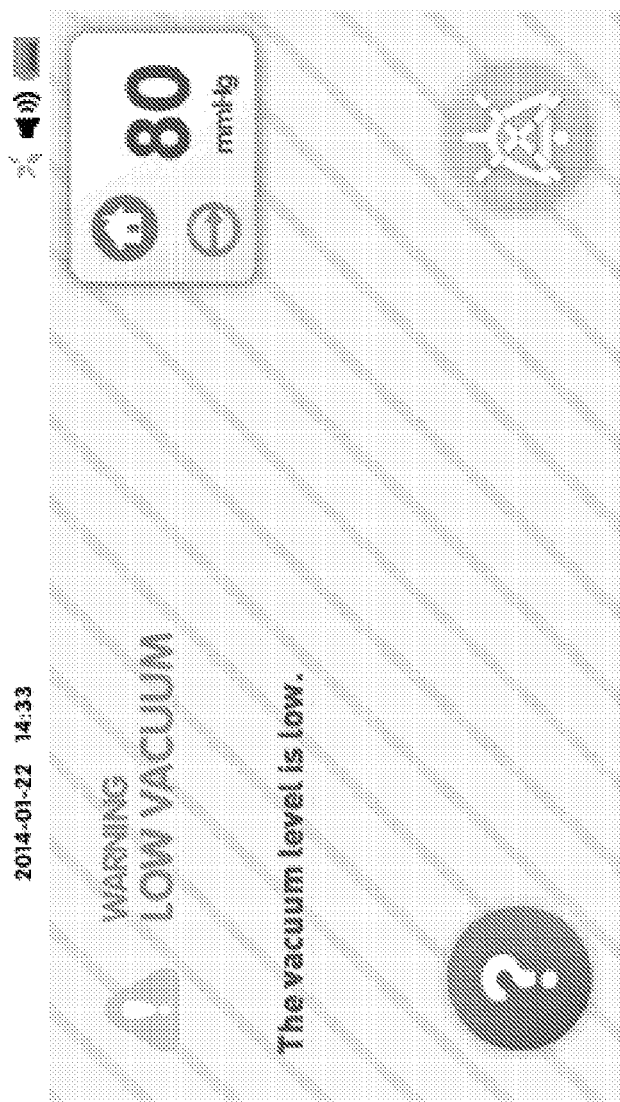

FIG. 6E illustrates a low vacuum alarm screen 600E according to some embodiments. As is illustrated, the description of the alarm is "LOW VACUUM" because the detected pressure at the wound is lower than the desired negative pressure by a threshold amount, such as −15 mmHg or another suitable value. Additionally or alternatively, low vacuum condition can be detected if there is a leak in the fluid flow path that persists for longer than threshold duration, such as 30 seconds or any other suitable value. The alarm may be resolved by checking the connections in the fluid flow path for leaks or checking the dressing for leaks. The pump assembly may continue to attempt to provide desired therapy to the wound. In some embodiments, the gauge 580 may be displayed on the screen 600E, as is explained below in connection with FIG. 6F. The alarm may be silenced.

Figure 6F:
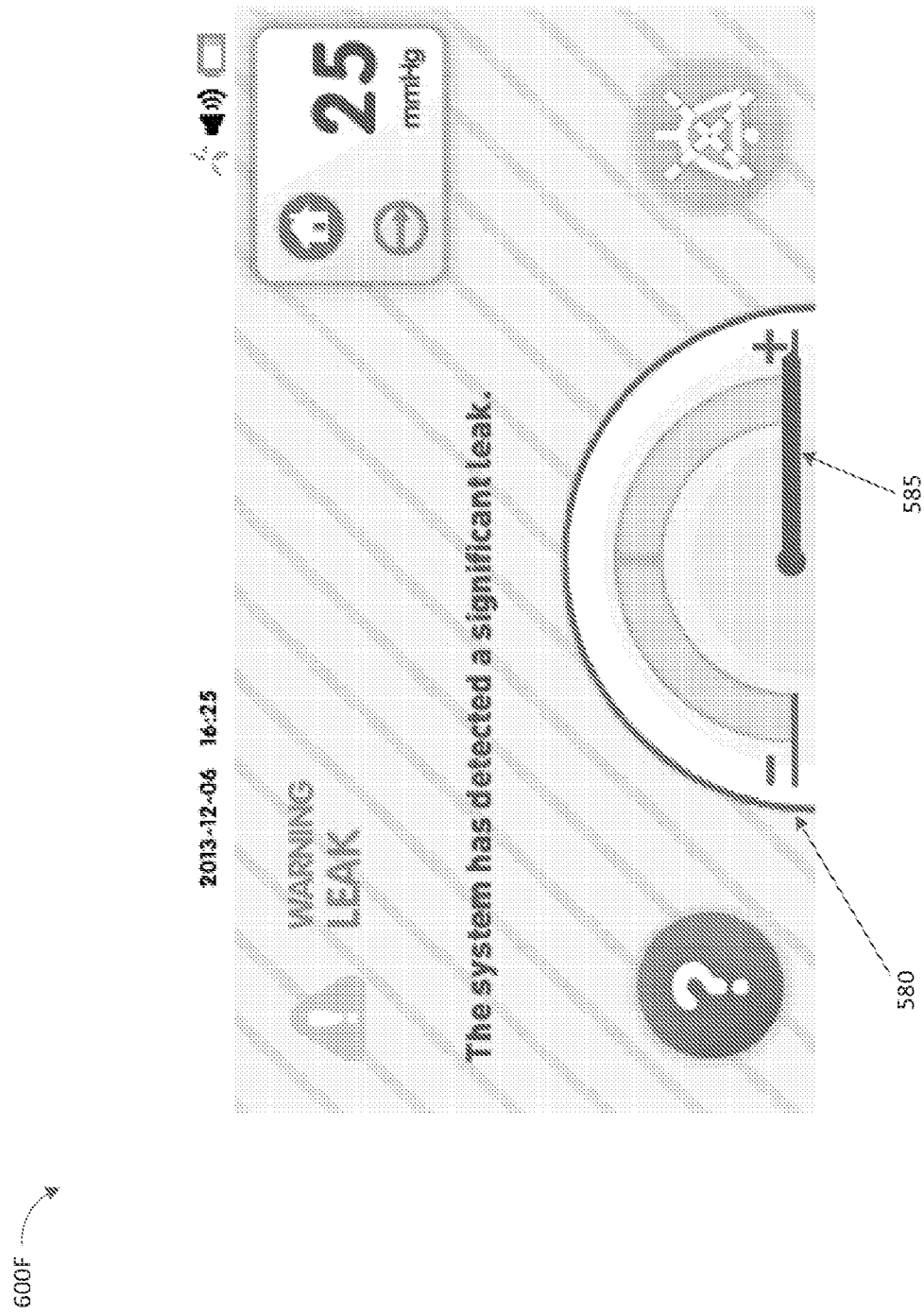

FIG. 6F illustrates a leak alarm screen 600F according to some embodiments. As is illustrated, the description of the alarm is "LEAK" because a significant leak (e.g., a leak that exceeds a certain threshold leak rate) has been detected for a threshold duration, such as for longer than 2 minutes or any other suitable value. As is illustrated, the leak alarm screen 600F includes the gauge 580 illustrating the leak rate detected in the fluid flow path. As is illustrated by the position of the needle 585, a high flow leak has been detected, which has triggered the leak alarm. The alarm may be resolved by checking the connections in the fluid flow path for leaks or checking the dressing for leaks. The gauge 580, which illustrates the detected leak rate, can assist in identifying and resolving leaks. The pump assembly may continue to attempt to provide desired therapy to the wound. The alarm may be silenced.

Figure 6G:
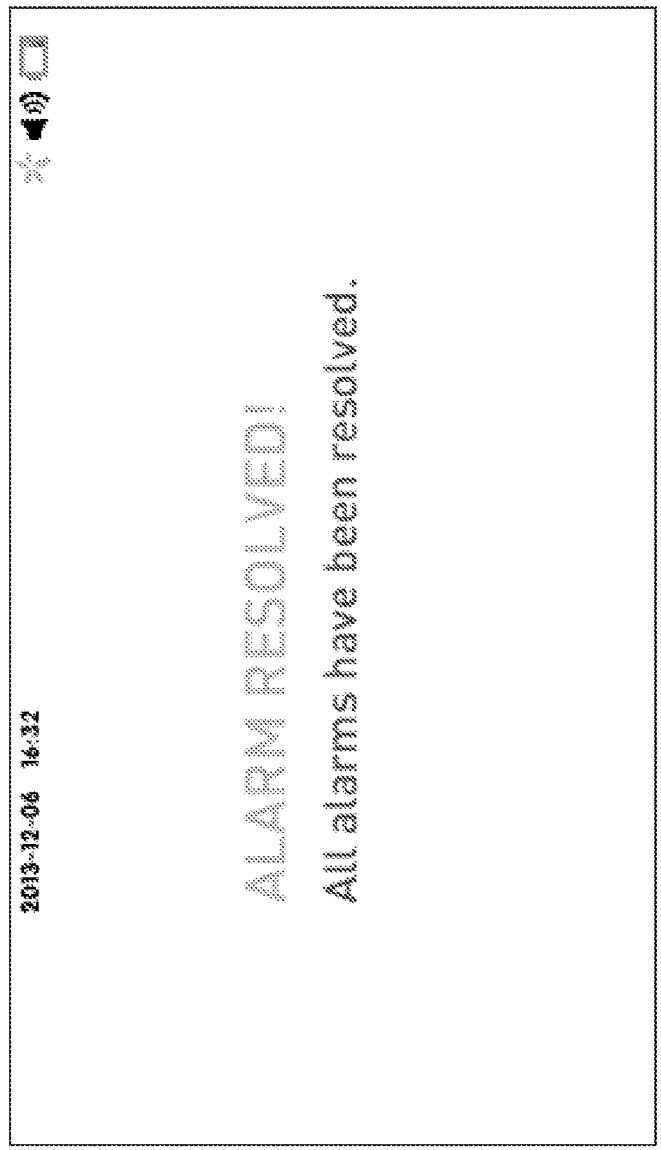

FIG. 6G illustrates an alarm resolved screen 600E according to some embodiments. Screen 600G can be displayed upon resolution of alarms detected by the therapy unit. Screen 600G can be displayed for a period of time and then be replaced by a therapy deliver screen. The alarm may be silenced.

Any of the screens depicted in FIGS. 6A-6G may include additional or alternative controls, indicators, messages, icons, and the like. In some embodiments, additional or alternative screens may be used for alerting the user to one or more alarms.

Delivery of Negative Pressure Wound Therapy

In some embodiments, the pump assembly controls the vacuum pump to deliver negative pressure therapy to a wound according to a selected or programmed protocol. Pump control can be performed by the pump control processor 370 alone or in combination with the processor 310. For example, as explained above, the user can select continuous operation at a desired pressure (or negative pressure setpoint). The pump assembly can activate the vacuum pump to reduce or draw down the pressure at the wound (e.g., under the dressing) to reach the setpoint. As explained below, the drawdown can be performed by increasing the negative pressure at the wound limited by a maximum change in negative pressure per unit time called compression, until the setpoint (or another selected pressure value as explained below) has been achieved. Wound drawdown can be defined as the period of time immediately after therapy has been initiated during which the wound has not yet achieved the setpoint. As explained below, at the end of this period when the setpoint is achieved, the flow rate in the fluid flow path should be below a leak (or high flow) threshold and above a low vacuum threshold, otherwise an appropriate alarm will be activated. As another example, the user can select intermittent operation between two desired pressures (or high and low pressure setpoints). The pump assembly can activate the vacuum pump to reduce or draw down the pressure at the wound to reach the high setpoint. Subsequently, the pump assembly can allow pressure at the wound to increase to reach the low setpoint. As explained below, decreasing and increasing negative pressure can be performed in accordance with the compression setting. As yet another example, compression can be used anytime there is a change in the pressure setpoint (which can include stopping delivery of negative pressure). In some embodiments, different compression settings can be used for setpoint changes that result in decreasing or increasing pressure at the wound. In various embodiments, compression setting can be adjusted while a pressure setpoint is being achieved.

Figure 7:
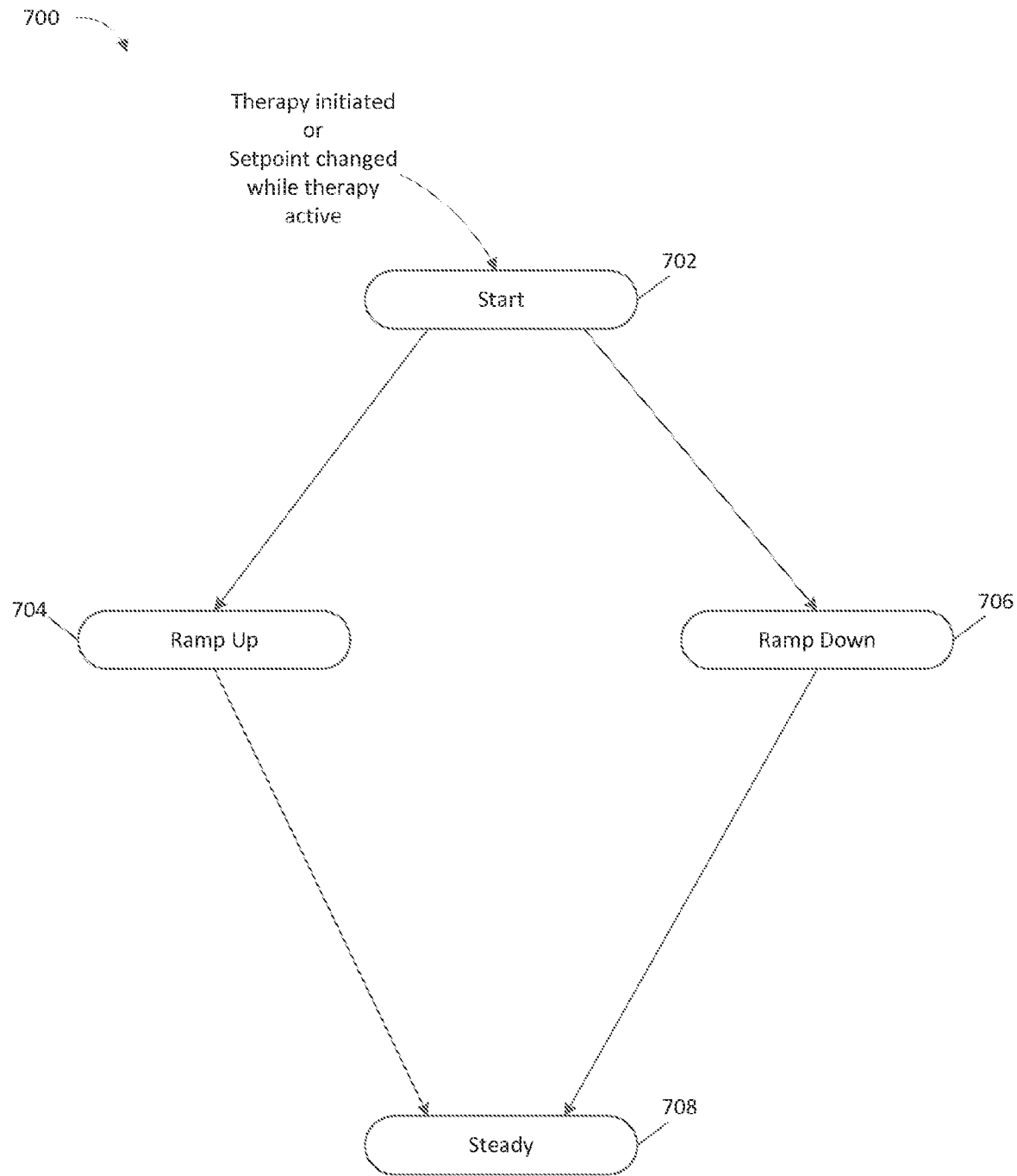
FIG. 7 illustrates a process of providing negative pressure wound therapy according to some embodiments.

FIG. 7 illustrates a process 700 for providing negative pressure wound therapy according to some embodiments. The process 700 can be executed by the pump control processor 370 alone or in combination with the processor 310. The process 700 can be periodically executed, such as for example every 100 milliseconds (or 10 times per second) or at any other suitable frequency. Alternatively or additionally, the process 700 can be continuously executed.

The process 700 can begin in block 702, which it can transition to when therapy is initiated or when the setpoint is changed while therapy is being delivered. In block 702, the process 700 compares wound pressure, which can be determined as explained below, to the setpoint. For example, the process 700 can subtract the wound pressure from the setpoint or vice versa. If the wound pressure is below the setpoint, the process 700 can transition to block 704. Conversely, if the wound pressure exceeds or is equal to the setpoint, the process 700 can transition to block 706.

In block 704 (pressure ramp up), the process 700 can increment a pump ramp setpoint by an amount that depends on the compression setting as explained below. The vacuum pump will then attempt to draw down (or make more negative) the wound pressure to reach the current value of the pump ramp setpoint. For example, a suitable pump drive signal, such as voltage or current signal, can be generated and supplied to the pump motor so as to increase the speed of the pump motor to achieve wound draw down. For purposes of efficiency, the pump motor can be driven using PWM or any other suitable method. The process 700 can continue incrementing the pump ramp setpoint until it reaches the setpoint selected by the user. The process 700 can transition to block 708 when the wound pressure has nearly reached or reached the setpoint, which can correspond to reaching steady state pressure under the wound dressing. For example, the process 700 can transition to block 708 when the wound pressure is within a ramp up threshold pressure of the setpoint, such as within 2 mmHg of the setpoint or within any other suitable value. In some embodiments, the pump ramp setpoint can be adaptively set to a higher negative pressure than the setpoint. For example, as is explained below, the device can detect presence of one or more leaks which result in a higher level of flow. Because this can cause loss of pressure at the wound, the device can compensate such loss of pressure by increasing the pump ramp setpoint above the setpoint. For instance, the device can set the pump ramp setpoint to be 1%, 2%, 5%, etc. more negative than the setpoint. In certain embodiments, the pump ramp setpoint can be adaptively set to a lower negative pressure (or more positive pressure) than the setpoint.

In block 706 (pressure ramp down), the process 700 can set the pump ramp setpoint to the setpoint selected by the user (or to another set value as explained above). The process 700 can deactivate the pump so that the wound pressure is allowed to decay, such as due to one or more leaks in the fluid flow path, to reach or almost reach the setpoint. This can be performed in accordance with the compression setting, such as for example, deactivating the pump for a first period of time and then activating the pump for a second period of time so that pressure at the wound increases according to the compression setting.

Additionally or alternatively, the process 700 can open and close one or more valves positioned in the fluid flow path to thereby admit ambient air or another gas into the fluid flow path in order to reach or almost reach the setpoint. This can be performed in accordance with the compression setting, such as for example, opening the one or more valves for a first period of time and then closing some or all of the one or more valves for a second period of time so that pressure at the wound increases according to the compression setting. Further, the process 700 can operate a positive pressure pump to increase the pressure at the wound. Also, the process 700 can utilize a reservoir configured to store air or gas to increase the pressure at the wound. This is described in more detail in U.S. Pat. No. 8,366,692, which is incorporated by reference in its entirety.

At this point, the process 700 can transition to block 708. For example, the process 700 can transition to block 708 when the wound pressure is within a ramp down threshold pressure of the setpoint, such as within 5 mmHg of the setpoint or within any other suitable value. In some cases, the ramp down threshold pressure can be the same as the ramp up threshold pressure. In some embodiments, the pump ramp setpoint can be adaptively set to a lower negative pressure than the setpoint. For example, as is explained below, the device can detect presence of one or more leaks which result in a higher level of flow. Because this can cause loss of pressure at the wound, the device can compensate such loss of pressure by decreasing the pump ramp setpoint below the setpoint. For instance, the device can set the pump ramp setpoint to be 1%, 2%, 5%, etc. less negative than the setpoint. In certain embodiments, the pump ramp setpoint can be adaptively set to a higher negative pressure (or more positive pressure) than the setpoint.

In block 708 (steady state), the pump ramp setpoint can be set to the setpoint selected by the user (or another suitable value). The process 700 can control the vacuum pump to maintain the desired negative pressure at the wound. One or more conditions, such as high vacuum, low vacuum, leak, and the like can be detected in block 708 as is explained below. If the user changes the setpoint to be more negative or more positive or if delivery of therapy is paused, the process 700 can transition to block 702.

In some embodiments, the pump assembly controls the vacuum pump to draw down the wound (e.g., as is explained above in connection with block 704) by utilizing compression. Using compression can be beneficial for avoiding rapid changes in wound pressure, which can minimize patient discomfort, reduce noise produced as a result of operating the pump, maintain efficient delivery of negative pressure, maintain efficient use of power (e.g., battery power), and the like. Compression can be executed by the process 700, which in turn can be implemented by the pump control processor 370 alone or in combination with the processor 310. Compression can correspond to the maximum desired increase or decrease in negative pressure at the wound per unit of time. Compression can be determined based on the negative pressure setpoint in the continuous mode or low and high negative pressure setpoints in the intermittent mode and selected compression setting (e.g., low, medium, or high) as explained above in connection with FIG. 5F.

Compression can be utilized when the wound is expected to experience a significant increase in negative pressure. This can occur when: (1) therapy is initiated on a deflated wound, and negative pressure will increase from zero or substantially zero to reach the pressure setpoint at the wound; (2) therapy is active in intermittent mode and during transitions from a low negative pressure setpoint to a high negative pressure setpoint, negative pressure will increase to reach the high pressure setpoint at the wound; (3) therapy is active in intermittent mode and during transitions from a high negative pressure setpoint to a low negative pressure setpoint, negative pressure will decrease to reach the low pressure setpoint at the wound; (4) therapy is active and the setpoint has been changed to a more negative pressure value, which will cause negative pressure to be increased to reach the higher pressure setpoint at the wound; (5) therapy is active and the setpoint has been changed to a more positive pressure value, which will cause negative pressure to be decreased to reach the lower pressure setpoint at the wound; and (6) therapy is active and is stopped or paused for a period of time, which will cause the pressure to be gradually restored to atmospheric pressure. Additional situations in which compression may be utilized include, for example, when a leak is introduced after seal has been achieved, which can cause negative pressure at the wound to rapidly drop and the vacuum pump to increase or ramp up delivery of negative pressure in an attempt to maintain pressure. Once the leak has been corrected, the pump would attempt to rapidly restore setpoint pressure at the wound according to the compression setting.

Compression can be achieved by maintaining a secondary negative pressure setpoint target that represents the negative pressure setpoint allowed by compression as a function of time. The secondary setpoint can correspond to the pump ramp setpoint. Secondary setpoint can be incremented or decremented based on the selected compression setting. Secondary setpoint can be incremented or decremented by a suitable amount every time process 700 is executed, such as 10 times a second or any other suitable frequency. For example, if low compression setting has been selected, the secondary setpoint can be incremented by −0.6 mmHg (or decremented by 0.6 mmHg), which can result in negative pressure ramp up (or ramp down) of no more than approximately −8 mmHg (or 8 mmHg) per second (assuming that pump rate is incremented 10 times a second, such as a result of executing the process 700). If medium compression setting has been selected, the secondary setpoint can be incremented by −2 mmHg (or decremented by 2 mmHg), which can result in negative pressure ramp up (or ramp down) of no more than approximately −20 mmHg (or 20 mmHg) per second. If high compression setting has been selected, the secondary setpoint can be incremented by −4 mmHg (or decremented by 4 mmHg), which can result is negative pressure ramp up (or ramp down) of no more than approximately −40 mmHg (or 40 mmHg) per second. These values are illustrative and any other suitable values can be used.

In some embodiments, the pump assembly monitors various parameters, such as pressure and rate of flow in the fluid flow path, in order to control the pump in connection with delivery of negative pressure wound therapy. Parameters monitoring and pump control can be performed by the pump control processor 370 alone or in combination with the processor 310. Monitoring the flow rate can be used, among other things, to ensure that therapy is properly delivered to the wound, to detect leakages, blockages, high pressure, and low vacuum, canister full, and the like.

The pump assembly can be configured to indirectly measure the flow rate in the fluid flow path. For example, the pump assembly can measure the speed (e.g., as frequency) of the vacuum pump motor by using a tachometer. Alternatively or additionally, the pump assembly can measure a level of activity or duty cycle of the pump using any suitable approach, such as by monitoring voltage or current supplied to the pump, sensing pump speed (e.g., by using a Hall sensor), measuring back EMF generated by the pump motor, and the like. Tachometer readings can be averaged in order to mitigate the effects of one or more errant readings. A number of most recent tachometer readings, such as over last 2.5 seconds or any other suitable time period, can be averaged to obtain short tachometer average. A number of less recent tachometer readings, such as aver the last 30 seconds or any other suitable time period, can be averaged to obtain long tachometer average. Short and long tachometer averages can be utilized for pump control. Additionally or alternatively, the pump assembly can directly measure the flow rate, such as by using a flow meter.

Flow rate can be estimated as the air or gas volume moving over the wound per unit of time normalized to standard temperature and standard pressure (e.g., 1 atm). Flow rate can be periodically computed, such as every 250 milliseconds or any other suitable time value, according to the following formula:

$$\text{Flow Rate} = \text{Slope} * \text{Tachometer} + \text{Intercept}$$

Tachometer is short tachometer average (e.g., in Hz) and Slope and intercept are constants that are based on the pressure setpoint. The values for Slope and Intercept can be determined for possible pressure setpoints (e.g., −25 mmHg, −4 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg) or a given vacuum pump type. The flow as a function of the pump speed may not be a best fit as a single line because the vacuum pump can be designed to be more efficient at lower flow rates. Because of this, slope and intercept values can be pre-computed for various setpoints and various pumps, Flow rate can be measured in standard liters per minute (SLPM) or any other suitable measurement unit. As explained below, the determined flow rate can be compared to various flow rate thresholds, such as blockage threshold, leakage threshold, and maximum flow rate threshold, to determine a presence of a particular condition, such as a blockage, leakage, over vacuum, etc.

In addition, the pump assembly can determine and monitor pressure in the flow path using one or more sensors. In some embodiments, the pump assembly includes a pressure sensor in or near the inlet 252 (or canister connection) of the pump assembly 230. This pressure sensor can measure the pressure in the canister (or in or near the dressing in a canisterless system). The arrangement of one or more pressure sensors in disclosed in U.S. Patent Publication No. 201570025482, which is incorporated by reference in its entirety. The pump assembly can continuously measure pressure in the canister, such as every millisecond or any other suitable duration. A suitable number of latest pressure sensor readings can be averaged to mitigate the effects of one or more errant readings.

Wound pressure can be estimated using the measured canister pressure and the pump speed. Because of presence of one or more leaks in the flow path, wound pressure may not be the same as canister pressure. For example, wound pressure may be lower or more positive than canister pressure. In some embodiments, wound pressure is estimated using the following formula:

$$\text{Wound Pressure} = \text{Canister Pressure} - (\text{Slope} * \text{Tachometer} + \text{Intercept})$$

Canister Pressure is averaged measured canister pressure. As explained above, Tachometer is short tachometer average and Slope and Intercept are constants that are based on the pressure setpoint. The values for Slope and Intercept are not necessarily same value as used above for determining the flow rate. Additionally or alternatively, wound pressure can be measured directly by a pressure sensor placed in the wound or near the wound or under the dressing.

Based on the determined flow rate, canister pressure, and wound pressure values, the pump assembly can monitor and detect various operating conditions. One or more of these conditions can be detected by the process 700 while the process in in block 708. Blockage in the fluid flow path can be determined by comparing the flow rate, as reflected by long tachometer average, to a particular blockage threshold over or during a period of time, such as 2 minutes or any other suitable duration. The blockage threshold can be selected or determined based on the particular pressure setpoint. That is, to detect blockage, the pump assembly can utilize a plurality of blockage thresholds corresponding to particular pressure setpoints. As explained above, the flow rate can be indirectly determined by detecting and monitoring the pump speed. Long tachometer average can be compared to the blockage threshold. Alternatively or additionally, short tachometer average or any other suitable measure of flow rate can be compared to the blockage threshold.

If the threshold is satisfied during a duration of a period of time, the pump assembly determines that there is a blockage in the fluid flow path and provides an indication (e.g., alarm screen). For example, to determine presence of a blockage, the pump assembly can determine whether the long tachometer average satisfies or exceeds the blockage threshold during a 2 minute period of time or during any other suitable period of time. Because long tachometer average may be updated at periodic time intervals due to periodic sampling of the tachometer, the pump assembly may compare the long tachometer average as it is being updated to the blockage threshold aver the 2 minute period of time. Blockage can be detected provided that each long tachometer average determined during the 2 minute interval satisfies or exceeds the blockage threshold. Alternatively or additionally, blockage can be detected if the majority of sampled long tachometer averages, such as 9 out of 10 or any other suitable number, satisfy or exceed the blockage threshold. Detected blockage may be cleared when the long tachometer average falls below the blockage threshold for a period of time, such as 5 seconds or any other suitable duration.

In some embodiments, blockage detection may be suspended while the process 700 is in block 706. That is, blockage detection can be configured to be suppressed or disabled when the therapy unit is in the ramp down state 706. Blockage detection can be enabled or re-enabled when the process transitions to another state, such as the steady state 708. In some embodiments, blockage detection can be disabled when the process 700 is in a state other than the ramp down state 706, such as when the process 700 is in the ramp up state 704, and re-enabled when the process 700 is in a state other than the steady state 708. In some embodiments, the process 700 can continuously monitor for a blockage condition, but when such conditions is detected, the process 700 can be configured to suppress the blockage alarm when in, for example, a pressure ramp down state.

When the pump is off, such as when intermittent therapy is applied with one of the pressure setpoints being set to zero, and negative pressure at the wound is expected to decrease (or become more positive) due to leaks, blockage can be detected by determining whether the pressure level at the wound is decreasing or decaying as expected. For example, the drop in pressure at the wound can be computed over a period of time, such as 30 seconds or any other suitable duration. A blockage may be present if the wound pressure at the end of the period of time has not decreased to satisfy (e.g., exceed) a pressure decay threshold.

The pump assembly can detect and provide indication of a low vacuum condition by determining whether the canister pressure satisfies (e.g., falls below or is more positive than) a low vacuum pressure threshold during a period of time, such as 30 seconds or any other suitable duration. The low vacuum pressure threshold can be selected or determined based on the pressure setpoint. As is explained above in connection with blockage detection, low vacuum detection may be suspended while the process 700 is in block 706. Detected low vacuum can be cleared when the canister pressure exceeds the low vacuum pressure threshold for a period of time, such as 5 seconds or any other suitable value. Alternatively or additionally, the pump assembly can compare the measured wound pressure with the low vacuum pressure threshold.

The pump assembly can detect and provide indication of a high vacuum condition by determining whether the canister pressure satisfies (e.g., exceeds) a particular high vacuum pressure threshold during a period of time, such as 30 seconds or any other suitable duration. The high vacuum pressure threshold can be selected or determined based on the pressure setpoint. As is explained above in connection with blockage detection, high vacuum detection may be suspended while the process 700 is in block 706. Detected high vacuum may be cleared by power cycling the pump assembly or by another other suitable means, such as by determining that the canister pressure falls below the high vacuum pressure threshold for a period of time, such as 5 seconds or any other suitable duration. Alternatively or additionally, the pump assembly can compare the measured wound pressure with the high vacuum pressure threshold.

The pump assembly can detect and provide indication of an over vacuum (or excessive vacuum) condition by determining whether the canister pressure satisfies (e.g., exceeds) an over vacuum threshold, such as −250 mmHg or any other suitable value, during a period of time, such as 2 seconds or any other duration. Detected over vacuum may be cleared by power cycling the pump assembly or by another other suitable means, such as by determining that the canister pressure falls below the over vacuum pressure threshold for a period of time, such as 5 seconds or any other suitable duration. Alternatively or additionally, the pump assembly can compare the wound pressure with the over vacuum threshold. As is explained above in connection with blockage detection, detection of over vacuum may be suspended while the process 700 is in block 706.

The pump assembly can detect and provide indication of a leak condition by determining whether the short tachometer average satisfies a leak threshold during a period of time, such as 2 minutes or any other suitable duration. The leak threshold can be selected or determined based on the pressure setpoint. For example, the pump assembly can determine whether the short tachometer average exceeds the leak threshold over a 2 minute period as the vacuum pump is attempting to reach and/or maintain the desired setpoint in the presence of one or more leaks. Alternatively or additionally, the pump assembly can compare the long tachometer average with the leak threshold. As is explained above in connection with blockage detection, leak detection may be suspended while the process 700 is in block 706. Detected leak may be cleared when the short tachometer average falls below the leak threshold for a period of time, such as 5 seconds or any other suitable duration. Alternatively or additionally, long tachometer average or any other suitable measure of flow rate can be compared to the leak threshold.

The pump assembly can detect and provide indication of a canister full condition. This determination can be made in when the process 700 is in block 708. First, the pump assembly can determine whether the short tachometer average is below the leak threshold and the canister pressure exceeds (or is more negative than) the low vacuum pressure thresholds is indicated by the short tachometer average being below the leak threshold, there are leak or leaks in the fluid flow path while there is no tow vacuum condition detected, as is indicated by canister pressure being above the low vacuum pressure threshold (e.g., canister pressure is normal). That is, the determination of canister pressure remaining at a normal level while presence of a significant leak in the fluid flow path has been detected (e.g., as indicated by pump speed being fairly low), provides an indication that the canister may be full (e.g., canister filter may be blocked).

Figure 8:
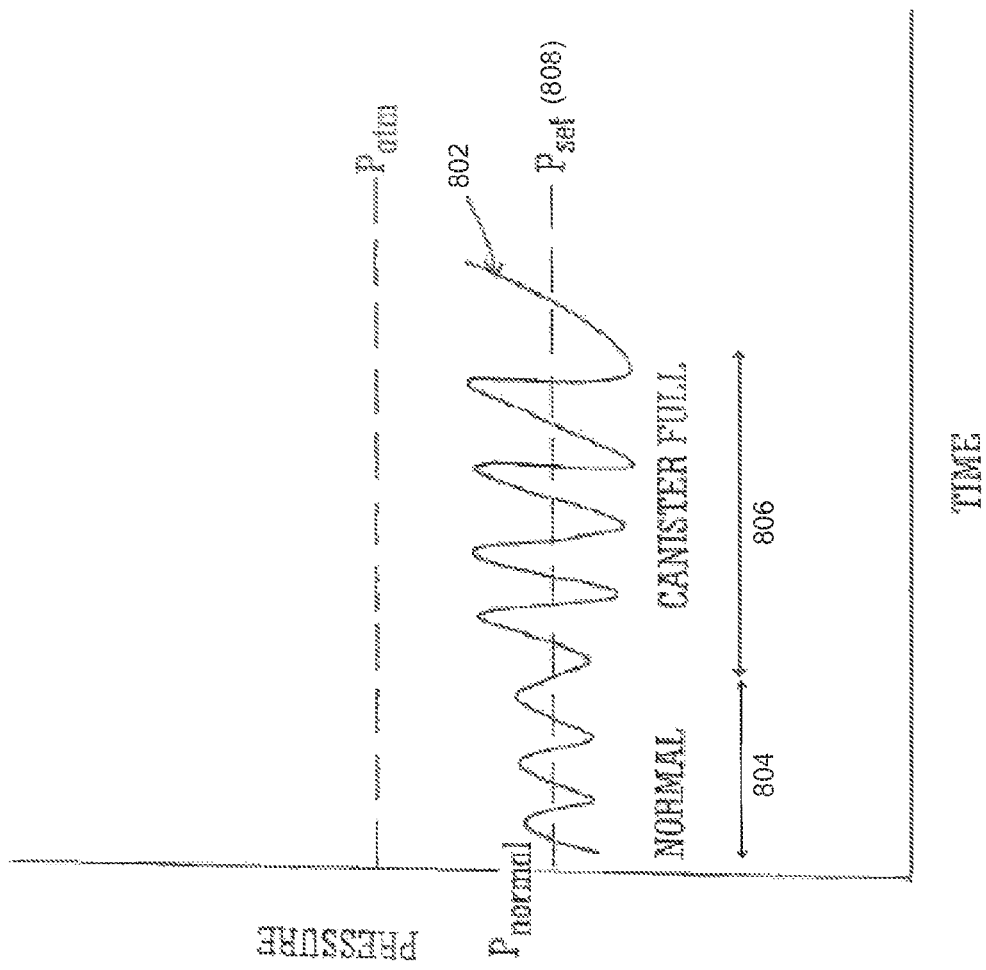
FIG. 8 illustrates pressure pulses according to some embodiments.

After it has been determined that the short tachometer average is below the leak threshold and the canister pressure exceeds the low vacuum pressure threshold, determination of Whether the canister if full is performed based at least in part on measuring characteristics of pressure pulses or signals in the fluid flow path. During operation, the pump generates pressure pulses or signals that are propagated through the fluid flow path. The pressure signals, which can be detected by a pressure sensor, are illustrated by the pressure curve 802 of FIG. 8 according to some embodiments. As is illustrated in region 804, pressure in the fluid flow path varies or oscillates around a particular pressure setpoint 808 during normal operation of the system. Region 806 illustrates pressure pulses in the flow path in presence of a blockage distal to the pump. For example, the canister (or dressing) becomes full and/or a canister (or dressing) filter is occluded or blocked.

As is illustrated in region 806, presence of a distal blockage causes a reduced volume to be seen upstream of the canister (or dressing), and the amplitude of the pressure pulses changes (e.g., increases). The frequency of a pressure signal also changes (e.g., slows down or decreases). Observed changes in one or more parameters of the pressure signal can be used to identify the type of distal blockage present, such as distinguish between canister (or dressing) full and other types of blockages in the fluid flow path. Changes in the amplitude of the pressure signal can be measured using a variety of techniques, such as by measuring peak-to-trough change. In certain embodiments, the changes in the pressure pulse signal can be magnified or enhanced by varying the pump speed, varying the cadence of the pump, such as by adjusting PWM parameters, and the like. Such adjustments of pump operation are not required but can be performed over short time duration and the changes can be small such that the operation of the system remains relatively unaffected. In some systems, such as in canisterless systems where a dressing is configured to absorb fluid removed from the wound, detection of a dressing full condition or dressing filter (which may be hydrophobic) occluded condition can be an equivalent to detection of canister full condition.

Canister full condition can be detected by collecting a plurality of pressure sensor readings, each performed over a time duration (e.g., 2 seconds or any other suitable duration which may be vary between sample periods), are collected. A number of readings of the plurality of readings, such as 25 sample periods out of 30 or any other suitable number, are checked to determine if each indicates that the canister is full. This can performed by determining maximum and minimum pressure values captured over the time duration of a particular sample period. The values can be voltage values, current values, or any other suitable values that correspond to pressure. A difference between maximum and minimum values for a particular sample period corresponds to peak-to-through pressure (which is indicative of change in pressure pulse amplitude). If it is determined that the peak-to-through pressure for a particular sample period exceeds a threshold pressure value, then the particular sample period indicates that the canister is full.

The threshold value can be any suitable pressure threshold, such as a value selected or determined based on the negative pressure setpoint and the current level of activity of the pump, which as explained above can be determined using short tachometer average (or long tachometer average or any other suitable measure of flow rate). For example, threshold values listed in Table 1 can be used for comparing to peak-to-through pressure. These values correspond to a particular pump motor and particular pressure sensor.

TABLE 1

Threshold values for detecting canister full condition

| Setpoint (in mmHg) | Tachometer Frequency (in Hz) | | | Peak-to-Through Pressure (in mV) | | |
|---|---|---|---|---|---|---|
| | Low | Med | High | Low | Med | High |
| 25 | 17 | 25 | <25 | 50 | 110 | 215 |
| 40 | 23 | 35 | <35 | 75 | 135 | 220 |
| 50 | 30 | 50 | <50 | 90 | 175 | 225 |
| 60 | 30 | 55 | <55 | 80 | 185 | 225 |
| 70 | 40 | 60 | <60 | 115 | 185 | 235 |
| 80 | 40 | 60 | <60 | 100 | 165 | 235 |
| 90 | 45 | 65 | <65 | 110 | 170 | 235 |
| 100 | 45 | 65 | <65 | 105 | 165 | 235 |
| 120 | 45 | 75 | <75 | 105 | 175 | 235 |
| 140 | 50 | 85 | <85 | 110 | 190 | 235 |
| 160 | 60 | 90 | <90 | 110 | 165 | 220 |
| 180 | 75 | 100 | <100 | 130 | 165 | 220 |
| 200 | 75 | 100 | <100 | 125 | 155 | 210 |

Canister full determination can be performed on a sliding window basis. For example, a sliding window of 25 out of 30 sample periods can be analyzed and if 25 sample periods are determined to indicate that the canister is full, the pump concludes that the canister (or dressing) is full. Assuming that the sample period is 2 seconds, using a sliding window of 25 out of 30 sample periods effectively results in determining whether change in pressure pulse amplitude exceeds the threshold for 60 seconds. If short tachometer average becomes greater than the leak threshold or canister pressure becomes less than the low vacuum pressure threshold, canister full detection can be suspended or terminated. For example, if a sliding window of 25 out of 30 sample periods with each sample period having duration of 2 seconds in used, 60 second timer for canister full detection can be reset when it has been determined that short tachometer average becomes greater than the leak threshold or canister pressure becomes less than the low vacuum pressure threshold. This can prevent generation of unnecessary and undesirable alarms.

Alternatively or additionally, canister full condition can be detected if a single sample period indicates that the canister is full. However, performing canister full detection using a plurality of sample periods can mitigate the effects of one or more transient conditions in the fluid flow path or one or more errant pressure readings. Alternatively or additionally, canister full detection can be performed by measuring the frequency of detected pressure signal and comparing the measured frequency to one or more suitable thresholds. As is explained above in connection with blockage detection, canister full detection may be suspended.

The pump assembly can perform leak check test, which may result in detection of a leak or low vacuum. If at any point during a time period that follows initiation of therapy, such as 45 seconds or any other suitable duration after therapy has been started, the short tachometer average rate falls below the leak threshold and process 700 has transitioned to block 708 (steady state), the leak check test has passed and suitable seal is deemed to have been achieved. That is, if pressure at the wound has reached the desired setpoint within the period of time and the flow rate (as indicated by the short tachometer average or any other suitable metric) does not satisfy or exceed the leak threshold, it is determined that the fluid flow path is suitably scaled and no significant leaks are present (e.g., the dressing has been properly placed and proper connections between pump assembly, canister, and dressing have been made). However, if the short tachometer average remains above the leak threshold at the end of the period of time, a leak is likely to be present, and the pump assembly indicates presence of a leak.

If at the end of the period of time, the process 700 remains in block 704 (or 706) and has not transitioned to block 708, the pump assembly determines whether the canister pressure satisfies or is above the low vacuum pressure threshold and the short tachometer average is below the leak threshold. If both of these conditions are met, it is determined that the fluid flow path is suitably sealed and no significant leaks are present. That is, even though the process 700 has not yet transitioned to block 708, which indicates that the setpoint has been reached or substantially reached, the pump is properly working toward establishing the negative pressure setpoint at the wound as is evidenced by the flow rate remaining below the leak threshold and the vacuum level remaining above the low vacuum threshold. Conversely, if the flow rate satisfies or exceeds the leak threshold, a leak is likely to be present, and the pump assembly indicates presence of a leak. If the low vacuum threshold is satisfied, the pump assembly indicates a low vacuum condition. Alternatively or additionally, long tachometer average or any other suitable measure of flow rate can be compared to the blockage threshold.

After leak check test has passed, a suitable seal can be deemed to have been achieved until therapy is paused. After therapy is restarted, leak check test can be performed. As is explained above in connection with blockage detection, leak check may be suspended.

In some embodiments, selecting or activating Y-connect feature (see FIG. 5A) for treatment of multiple wounds, can alter or modify detection of one or more conditions, such as blockages, leaks, canister full condition, and the like. Activating the Y connect feature can adjust one or more of various thresholds described above. For example, activating the Y-connect feature can decrease sensitivity of blockage detection by increasing the blockage threshold, which is used for blockage detection as explained above. The blockage threshold can be increased by a suitable amount, such as doubled.

In additional or alternative embodiments, multiple pressure sensors can be placed in the fluid flow path to facilitate detection of one or more of the above-described conditions. For example, in addition to or instead of the pressure sensor being placed in the pump inlet, a pressure sensor can be placed in the wound or under the dressing to directly determine the wound pressure. Measuring pressure at different locations in the fluid flow path, such as in the canister and at the wound, can facilitate detection of blockages, leaks, canister full condition, and the like. Multiple lumens can be utilized for connecting fluid flow path elements, such as pressure sensors, canister, pump assembly, dressing, and the like. Canister full condition can be detected by placing a sensor, such as capacitive sensor, in the canister. In some embodiments, in order to prevent occurrence of over vacuum, the maximum pressure supplied by the pump can be limited mechanically or electrically. For example, a pump drive signal, such as voltage or current supplied to the pump, can be limited not exceed a maximum flow rate threshold, such as 1.6 liters/min or any other suitable value. Additional details of flow rate detection and pump control are provided in U.S. Patent Publication No. 2013/0150813, which is incorporated by reference in its entirety.

In some embodiments, one or more flow sensors and/or flow meters can be used to directly measure the fluid flow. In some embodiments, the pump assembly can utilize one or more of the above-described techniques in parallel to control the pump and to detect various conditions. The pump assembly can be configured to suitably arbitrate between using parameters determined by different techniques. For example, the pump assembly can arbitrate between flow rates determined indirectly, such as based on the pump speed as measured by a tachometer, and directly, such as by using a flow meter. In certain embodiments, the pump assembly can indirectly determine the flow rate and resort to direct determination of the flow rate when needed, such as when indirectly determined flow rate is perceived to be inaccurate or unreliable.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Although the present disclosure includes certain embodiments, examples and applications, it will be understood by diose skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. An apparatus for applying negative pressure therapy to a wound, the apparatus comprising:
   a source of negative pressure configured to be in fluidic communication with a wound dressing covering the wound, the source of negative pressure configured to aspirate fluid from the wound via a fluid flow path;
   a pressure sensor configured to measure pressure in the fluid flow path;
   a controller programmed to operate the source of negative pressure to achieve a target pressure in the fluid flow path, the controller further programmed to:
      determine a pressure difference between a current pressure in the fluid flow path measured by the pressure sensor and the target pressure, the target pressure being more positive than the current pressure;
      based on the pressure difference and a compression setting, determine an intermediate pressure that is more positive than the current pressure and more negative than the target pressure; and
      operate the source of negative pressure by turning off the source of negative pressure for a duration of time to attain the intermediate pressure in the fluid flow path and then operating the source of negative pressure to attain the target pressure in the fluid flow path.

2. The apparatus of claim 1, wherein the controller is programmed to operate the source of negative pressure by turning off the source of negative pressure for the duration of time to attain the intermediate pressure in the fluid flow path and then activating the source of negative pressure to attain the target pressure in the fluid flow path, the duration of time depending on the compression setting.

3. The apparatus of claim 1, wherein the controller is further programmed to:
   determine a pressure increment based on the compression setting; and
   set the intermediate pressure to a sum of the current pressure and the pressure increment.

4. The apparatus of claim 3, wherein the controller is further programmed to, in response to determining that the intermediate pressure has been attained in the fluid flow path, update the intermediate pressure to be equal to a sum of a previous intermediate pressure setting and the pressure increment.

5. The apparatus of claim 3, wherein the controller is further programmed to, in response to determining that the intermediate pressure has been attained in the fluid flow path, redetermine the pressure increment and update the intermediate pressure to be equal to a sum of a previous intermediate pressure and the redetermined pressure increment.

6. The apparatus of claim 1, wherein the controller is programmed to set the compression setting according to a user selection.

7. A method of operating a negative pressure apparatus, the method comprising:
   measuring pressure in a fluid flow path comprising a source of negative pressure configured to be in fluidic communication with a wound dressing covering a wound;
   determining a pressure difference between a current pressure in the fluid flow path and a target pressure, the target pressure being more positive than the current pressure;
   based on the pressure difference and a compression setting, determining an intermediate pressure that is more positive than the current pressure and more negative than the target pressure; and
   operating the source of negative pressure by turning off the source of negative pressure for a duration of time to attain the intermediate pressure in the fluid flow path and then operating the source of negative pressure to attain the target pressure in the fluid flow path,
   wherein the method is performed by a controller.

8. The method of claim 7, wherein operating the source of negative pressure to attain the target pressure in the fluid flow path comprises activating the source of negative pressure to attain the target pressure in the fluid flow path, the duration of time depending on the compression setting.

9. The method of claim 7, further comprising:
   determining a pressure increment based on the compression setting; and
   setting the intermediate pressure to a sum of the current pressure and the pressure increment.

10. The method of claim 9, further comprising in response to determining that the intermediate pressure has been attained in the fluid flow path, updating the intermediate pressure to be equal to a sum of a previous intermediate pressure and the pressure increment.

11. The method of claim 9, further comprising in response to determining that the intermediate pressure has been attained in the fluid flow path, redetermining the pressure increment and updating the intermediate pressure to be equal to a sum of a previous intermediate pressure and the redetermined pressure increment.

12. The method of claim 7, further comprising setting the compression setting according to a user selection.

13. The method of claim 12, further comprising causing a touch screen display to display a menu configured to permit a user to select the compression setting.

14. The method of claim 7, wherein turning off the source of negative pressure for the duration of time is performed during a transition from a first negative pressure to a second negative pressure more positive than the first negative pressure.

15. The method of claim 9, wherein determining the pressure increment comprises selecting the pressure increment according to the compression setting.

16. The apparatus of claim 1, wherein the controller is programmed to turn off the source of negative pressure for the duration of time during a transition from a first negative pressure to a second negative pressure more positive than the first negative pressure.

17. The apparatus of claim 3, wherein the controller is programmed to select the pressure increment according to the compression setting, and wherein when the compression setting is a first setting, the pressure increment that is selected is smaller than another pressure increment that is selected by the controller when the compression setting is a second setting different from the first setting.

18. The apparatus of claim 6, further comprising a touch screen display, and wherein the controller is further programmed to cause the touch screen display to display a menu configured to permit a user to select the compression setting.

19. The apparatus of claim 1, wherein the controller is further programmed to select the compression setting from a plurality of compression settings.

20. The apparatus of claim 19, wherein the plurality of compression settings comprises a low compression setting, a medium compression setting, and a high compression setting.

\* \* \* \* \*

UNITED STATES PATENT AND TRADEMARK OFFICE
CERTIFICATE OF CORRECTION

PATENT NO. : 10,828,401 B2  
APPLICATION NO. : 15/757467  
DATED : November 10, 2020  
INVENTOR(S) : William W. Gregory et al.

Page 1 of 2

It is certified that error appears in the above-identified patent and that said Letters Patent is hereby corrected as shown below:

In the Specification

In Column 1, Line 14, delete "TMP" and insert --TNP--.

In Column 6, Line 23, delete "TNT" and insert --TNP--.

In Column 8, Line 43, delete "END," and insert --DVD,--.

In Column 9, Line 4, delete "Input," and insert --Input--.

In Column 9, Line 59, delete "a" and insert --as--.

In Column 10, Line 36, after "control" insert --a--.

In Column 10, Line 40, delete "371" and insert --370--.

In Column 10, Line 56, delete "connectivity." and insert --connectivity,--.

In Column 13, Line 67, delete "500C" and insert --500B--.

In Column 14, Line 42, delete "tinier" and insert --timer--.

In Column 14, Line 58, delete "scaled)." and insert --sealed).--.

In Column 15, Line 37, delete "500E" and insert --500F--.

In Column 15, Line 45, delete "500C" and insert --500G--.

In Column 16, Line 17, delete "500C" and insert --500G--.

Signed and Sealed this  
Sixteenth Day of March, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,828,401 B2

In Column 18, Line 28, delete "600E" and insert --600G--.

In Column 22, Line 10, delete "aver" and insert --over--.

In Column 22, Line 24 (approx.), delete "intercept" and insert --Intercept--.

In Column 22, Line 27 (approx.), delete "-4" and insert -- -40--.

In Column 22, Line 29 (approx.), delete "or" and insert --for--.

In Column 22, Line 34 (approx.), delete "pumps," and insert --pumps.--.

In Column 22, Line 50 (approx.), delete "201570025482," and insert --2015/0025482,--.

In Column 23, Line 37, delete "aver" and insert --over--.

In Column 25, Line 12, delete "thresholds" and insert --threshold. As--.

In Column 25, Line 14, delete "tow" and insert --low--.

In Column 25, Line 26, delete "Whether" and insert --whether--.

In Column 27, Line 21, delete "scaled" and insert --sealed--.

In Column 27, Line 50, delete "cheek" and insert --check--.

In Column 27, Line 59, delete "Y connect" and insert --Y-connect--.

In Column 28, Line 55, delete "embodiment" and insert --embodiment,--.

In Column 29, Line 1, before "any" insert --to--.

In Column 29, Line 38, delete "diose" and insert --those--.

In the Claims

In Column 30, Line 24, Claim 4, after "intermediate pressure" delete "setting".